(12) United States Patent
Borgos

(10) Patent No.: US 8,360,985 B2
(45) Date of Patent: Jan. 29, 2013

(54) OPTICAL VITAL SIGN DETECTION METHOD AND MEASUREMENT DEVICE

(75) Inventor: John Borgos, Shoreview, MN (US)

(73) Assignee: Tarilian Laser Technologies, Limited, Hertsfordshire (GB)

(*) Notice: Subject to any disclaimer, the term of this patent is extended or adjusted under 35 U.S.C. 154(b) by 1056 days.

(21) Appl. No.: 11/752,724

(22) Filed: May 23, 2007

(65) Prior Publication Data

US 2007/0276265 A1 Nov. 29, 2007

Related U.S. Application Data

(60) Provisional application No. 60/802,810, filed on May 24, 2006, provisional application No. 60/874,665, filed on Dec. 13, 2006, provisional application No. 60/898,269, filed on Jan. 31, 2007.

(51) Int. Cl.
*A61B 5/02* (2006.01)
(52) U.S. Cl. ........................................ 600/500; 600/502
(58) Field of Classification Search .................. 600/500; 356/450, 498, 482, 486, 614; 73/800
See application file for complete search history.

(56) References Cited

U.S. PATENT DOCUMENTS

| | | |
|---|---|---|
| 3,517,999 A | 6/1970 | Weaver |
| 4,163,397 A | 8/1979 | Harmer |
| 4,297,684 A | 10/1981 | Butter |
| 4,336,978 A | 6/1982 | Suzuki |
| 4,409,983 A | 10/1983 | Albert |
| 4,421,979 A | 12/1983 | Asawa et al. |
| 4,701,017 A | 10/1987 | Kookootsedes |
| 4,750,796 A | 6/1988 | Shibata et al. |
| 4,798,445 A | 1/1989 | Yamamoto et al. |
| 4,822,135 A | 4/1989 | Seaver |
| 4,830,461 A | 5/1989 | Ishiharada et al. |
| 4,915,473 A * | 4/1990 | Haese et al. ................ 385/13 |
| 4,937,029 A | 6/1990 | Ishiharada et al. |

(Continued)

FOREIGN PATENT DOCUMENTS

| | | |
|---|---|---|
| EP | 0348224 | 12/1989 |
| EP | 1484010 | 12/2004 |

(Continued)

OTHER PUBLICATIONS

International Search and Written Opinion mailed Dec. 3, 2007 in PCT/US2007/069545, 27 pages.

(Continued)

*Primary Examiner* — Michael Kahelin
*Assistant Examiner* — Tho Tran
(74) *Attorney, Agent, or Firm* — Fish & Richardson P.C.

(57) ABSTRACT

A vital sign measurement device includes a sensor fixation device, an optical sensing system, and an output unit. The sensor fixation device is adapted to be placed against an anatomical location of a subject, within which is an artery. The optical sensing system includes an optical source, an optical refractor, and an optical detector, all of which are held by the sensor fixation device and move with movement of the sensor fixation device. The optical sensing system is positioned with respect to the sensor fixation device to sense movement corresponding to an arterial pulse when the sensor fixation device is placed against the anatomical location of the subject. The optical sensing system can sense an arterial pulse from the movement, bending, or compression of at least one portion of the optical sensing system relative to other portions of the optical sensing system resulting in a change in an optical signal received by the optical detector. The output unit receives, from the optical sensing system, an input indicative of movement corresponding to an arterial pulse and generates, using the input, a measure of the vital sign.

23 Claims, 21 Drawing Sheets

U.S. PATENT DOCUMENTS

| | | | |
|---|---|---|---|
| 5,039,617 A * | 8/1991 | McDonald et al. | ............. 436/69 |
| 5,088,501 A | 2/1992 | Niewisch | |
| 5,089,697 A | 2/1992 | Prohaska | |
| 5,107,847 A | 4/1992 | Knute et al. | |
| 5,138,152 A | 8/1992 | Botting | |
| 5,144,689 A | 9/1992 | Lovely | |
| 5,154,680 A | 10/1992 | Drzewiecki et al. | |
| 5,158,091 A | 10/1992 | Butterfield et al. | |
| 5,165,416 A | 11/1992 | Shinoda et al. | |
| 5,183,056 A | 2/1993 | Dalen et al. | |
| 5,212,379 A | 5/1993 | Nafarrate et al. | |
| 5,241,300 A | 8/1993 | Buschmann | |
| 5,276,322 A | 1/1994 | Carome | |
| 5,291,013 A * | 3/1994 | Nafarrate et al. | ........ 250/227.14 |
| 5,309,916 A | 5/1994 | Hatschek | |
| 5,363,458 A | 11/1994 | Pan et al. | |
| 5,365,354 A * | 11/1994 | Jannson et al. | ................. 359/15 |
| 5,436,444 A | 7/1995 | Rawson | |
| 5,534,000 A | 7/1996 | Bruce | |
| 5,604,318 A | 2/1997 | Fasshauer | |
| 5,711,291 A | 1/1998 | Takaki | |
| 5,840,036 A | 11/1998 | Voith | |
| 6,052,613 A | 4/2000 | Takaki | |
| 6,290,650 B1 * | 9/2001 | Butterfield et al. | ........... 600/485 |
| 6,322,515 B1 | 11/2001 | Goor et al. | |
| 6,443,906 B1 | 9/2002 | Ting et al. | |
| 6,490,931 B1 | 12/2002 | Fernald et al. | |
| 6,491,647 B1 | 12/2002 | Bridger et al. | |
| 6,498,652 B1 | 12/2002 | Varshneya et al. | |
| 6,533,729 B1 | 3/2003 | Khair et al. | |
| 6,763,256 B2 | 7/2004 | Kimball et al. | |
| 6,788,295 B1 | 9/2004 | Inkster | |
| 6,816,266 B2 | 11/2004 | Varshneya et al. | |
| 6,820,489 B2 | 11/2004 | Fernald et al. | |
| 6,918,879 B2 | 7/2005 | Ting et al. | |
| 7,463,796 B2 | 12/2008 | Borgos et al. | |
| 7,657,135 B2 | 2/2010 | Borgos et al. | |
| 7,822,299 B2 | 10/2010 | Borgos et al. | |
| 8,111,953 B2 | 2/2012 | Borgos et al. | |
| 2002/0095092 A1 | 7/2002 | Kondo et al. | |
| 2003/0004421 A1 | 1/2003 | Ting et al. | |
| 2003/0212316 A1 | 11/2003 | Leiden et al. | |
| 2006/0278240 A1 * | 12/2006 | Spillman et al. | ............. 128/898 |
| 2007/0142715 A1 | 6/2007 | Banet et al. | |
| 2007/0185393 A1 | 8/2007 | Zhou et al. | |
| 2007/0276261 A1 | 11/2007 | Banet et al. | |
| 2007/0276262 A1 | 11/2007 | Banet et al. | |
| 2007/0276632 A1 | 11/2007 | Banet et al. | |
| 2007/0287927 A1 | 12/2007 | Borgos | |
| 2008/0181556 A1 | 7/2008 | Borgos et al. | |
| 2008/0183053 A1 | 7/2008 | Borgos et al. | |
| 2008/0306393 A1 | 12/2008 | Ting et al. | |
| 2011/0213254 A1 | 9/2011 | Ting | |

FOREIGN PATENT DOCUMENTS

| | | |
|---|---|---|
| JP | 08-280638 | 10/1996 |
| JP | 08 285709 | 11/1996 |
| JP | 09-152308 | 6/1997 |
| SU | 1219047 | 3/1986 |
| WO | 96/08197 | 3/1996 |
| WO | WO2004/046869 | 6/2004 |
| WO | 2007/140210 | 12/2007 |
| WO | 2008/094340 | 8/2008 |

OTHER PUBLICATIONS

Ulyanov S. et al. "Speckle Interferometry for Biotissue Vibration Measurement" *Optical Engineering*, 1994. 33(3): 908-914.

International Preliminary Report on Patentability received in PCT/US2007/069545, mailed Dec. 11, 2008, 8 pages.

Hong et al, "Fiber-optic transducer for blood pressure measurements" Nov. 4, 1988, pp. 810-811.

Gagnadre et al. "Fibre optic sensor for physiological parameters" Electronics Letters, Oct. 15, 1998, pp. 1991-1993.

International Preliminary Report on Patentability in PCT/US2007/85397 mailed Aug. 13, 2009, 10 pages.

International Search Report and Written Opinion for Application No. PCT/US2007/085397, mailed Sep. 4, 2008, 17 pages.

European Office Action in European Application No. 12158791.9, dated May 14, 2012, 5 pages.

Chinese Office Action in Chinese Application No. 201010623648.6, dated Jan. 30, 2012, 11 pages.

Japanese Office Action in Japanese Application No. 2009-512284, dated Jul. 17, 2012, 2 pages.

Malaysian Search Report in Malaysian Application No. PI 20084762, dated Aug. 15, 2012, 3 pages.

* cited by examiner

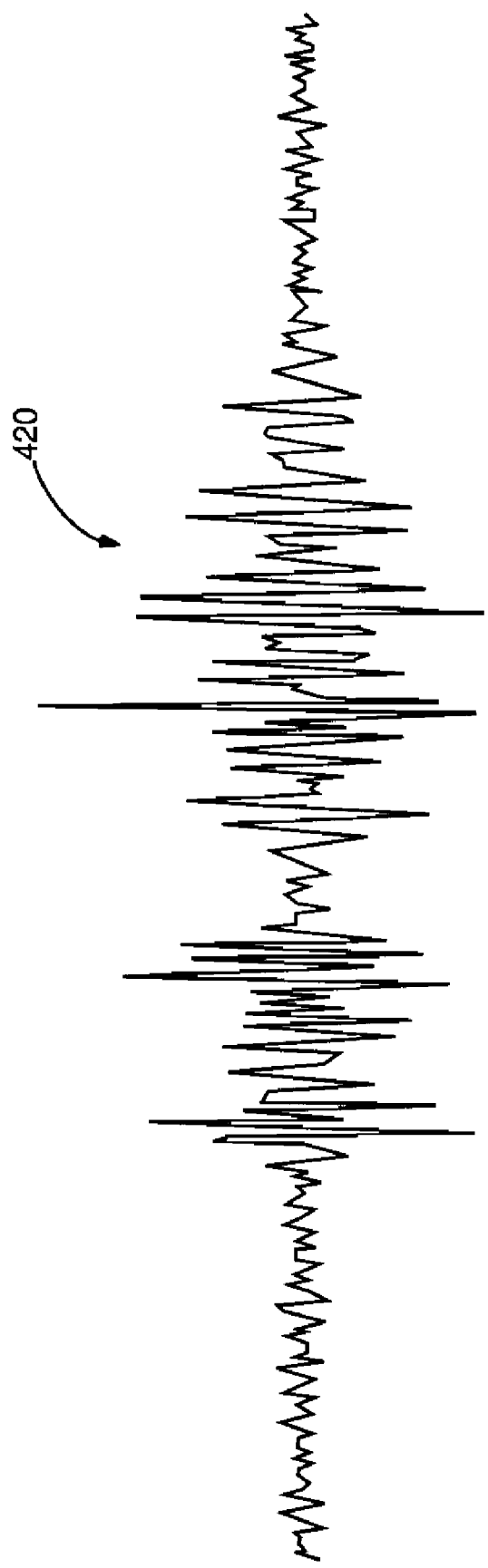

OPTICAL VITAL SIGN DETECTION METHOD AND MEASUREMENT DEVICE

CROSS-REFERENCE TO RELATED APPLICATIONS

This application claims the benefit of and priority to U.S. Provisional Patent Application Ser. No. 60/802,810, filed on May 24, 2006, U.S. Provisional Patent Application Ser. No. 60/874,665, filed on Dec. 13, 2006, and U.S. Provisional Patent Application Ser. No. 60/898,269, filed on Jan. 31, 2007, all of which are herein incorporated by reference in their entirety.

TECHNICAL FIELD

This invention relates to detecting vital signs, and more particularly to a vital sign measurement device.

BACKGROUND

Blood pressure refers to the force exerted by circulating blood on the walls of blood vessels and constitutes one of the principal vital signs. The systolic pressure is the peak pressure in the arteries, which occurs near the beginning of the cardiac cycle. The diastolic pressure is the lowest pressure, which is at the resting phase of the cardiac cycle. The average pressure throughout the cardiac cycle is reported as the mean arterial pressure. The pulse pressure reflects the difference between the maximum and minimum pressures measured.

Blood pressures can be measured invasively (by penetrating the skin and measuring inside the blood vessels) or non-invasively. The former is usually restricted to a hospital setting. The non-invasive auscultatory and oscillometric methods are simpler and quicker than invasive methods, have less complications, and are less unpleasant and less painful for the patient. Non-invasive measurement methods are more commonly used for routine examinations and monitoring.

The auscultatory method typically uses a stethoscope and a sphygmomanometer. An inflatable cuff is placed around the upper arm at roughly the same vertical height as the heart and pneumatically connected to a mercury manometer or aneroid gauge. The mercury manometer measures the height of a column of mercury, giving an absolute cuff pressure measurement without need for calibration and consequently not subject to the errors and drift of calibration which affect other pressure gauges. The cuff is inflated manually by repeatedly squeezing a rubber bulb until the brachial artery is completely occluded. While listening with the stethoscope over the brachial artery distal to the pressurized cuff, the examiner slowly releases the pressure in the cuff. When blood just starts to flow in the artery, the turbulent flow creates a "whooshing" or pounding sound (first Korotkoff sounds). The pressure at which this sound is first heard is the systolic blood pressure. The cuff pressure is further released until no sound can be heard (fifth Korotkoff sound), at the diastolic blood pressure.

Oscillometric methods are sometimes used for continuous monitoring and sometimes for making a single measurement. The equipment is functionally similar to that of the auscultatory method but does not rely on the use of a stethoscope and an examiner's ear. Instead, the detection means is a pressure sensor that is pneumatically connected to the cuff and registers the (relatively small) oscillations in cuff pressure that are synchronous with the arterial pressure waveform. The first oscillation in cuff pressure does not occur at the systolic pressure, but at a cuff pressure substantially above systolic pressure. The cuff is initially inflated to a pressure in excess of the systolic blood pressure. The cuff pressure is then gradually reduced. The values of systolic and diastolic pressure are calculated from the different oscillation amplitudes that occur at various cuff pressures by the use of an algorithm. Algorithms used to calculate systolic and diastolic pressure often use experimentally obtained coefficients aimed at matching the oscillometric results to results obtained by using the auscultatory method as well as possible.

SUMMARY

In some aspects, a vital sign measurement device includes a sensor fixation device, an optical sensing system, and an output unit. The sensor fixation device is adapted to be placed against an anatomical location of a subject, within which is an artery. The optical sensing system includes an optical source, an optical refractor, and an optical detector, all of which are held by the sensor fixation device and move with movement of the sensor fixation device. The optical sensing system is positioned with respect to the sensor fixation device to sense movement corresponding to an arterial pulse when the sensor fixation device is placed against the anatomical location of the subject. The optical sensing system can sense an arterial pulse from the movement, bending, or compression of at least one portion of the optical sensing system relative to other portions of the optical sensing system, which can result in a change in an optical signal received by the optical detector. The output unit receives, from the optical sensing system, an input indicative of movement corresponding to an arterial pulse and generates, using the input, a measure of the vital sign.

In some implementations, the sensor fixation device can be an inflatable cuff. In some implementations, the vital sign measurement device can include pressure sensor to detect a pressure applied to the anatomical location. In some implementations, the output unit can receive, from a pressure sensor, a pressure input indicative of the pressure applied to the anatomical location and generate a vital sign using the input from the optical sensing system and the pressure input.

In some implementations, the anatomical location of the subject the body can be an upper arm and the sensor fixation device can be configured so that the optical sensing system is positionable to sense movement due to a pulse of a brachial artery. In some implementations, the anatomical location of the subject can be a wrist and the sensor fixation device can be configured so that the optical sensing system is positionable to sense movement due to a pulse of a radial artery. In some implementations, the anatomical location of the subject can be an ankle, and the sensor fixation device can be configured so that the optical sensing system is positionable to sense movement due to a pulse of one or more arteries in the ankle.

In some implementations, optical refractor can be a compressible waveguide and/or a flexible waveguide. In some implementations, the optical refractor can be a diffuser.

In some implementations, the optical source and the optical refractor can be configured to produce a speckle pattern output. The optical detector can be positioned to detect a portion of the speckle pattern output and generate therefrom a signal indicative of optical energy received within the detected portion of the speckle pattern output. In some implementations, the optical sensor can include a spatial optical occluder component that prevents the optical detector from receiving a portion of the speckle pattern output. In some implementations, the optical detector can have an optical energy receiving portion having a smaller surface area than the speckle pattern output. For example, the surface area of the optical energy receiving portion can be less than 100 times an average speckle size.

In some implementations, the optical source can be a coherent light source (e.g., a laser).

In some implementations, the vital sign can be at least one of a heart rate, an arterial pulse waveform, a systolic blood pressure, a diastolic blood pressure, a mean arterial blood pressure, a pulse pressure, and an arterial compliance.

In some implementations, the output unit can generate a measure of the vital sign using a signal indicative of the optical signal received by the optical detector.

In some implementations, the vital sign measurement device can include display to depict a vital sign measurement generated by the output unit. In some implementations, the vital sign measurement device can include an alarm system to produce a human detectable signal when a vital sign measurement generated by the output unit meets a predetermined criteria.

In some implementations, the vital sign measurement device can include a spring attached to at least a portion of the optical sensing system to counter a force from the arterial pulse and to return the optical sensing system to an initial state after the arterial pulse.

In some implementations, the vital sign measurement device can include a pressure imparting device adapted to be placed against a second anatomical location of a subject proximal to the anatomical location of the sensor fixation device to allow for arterial pulse detection by the optical sensing system at a position distal to and separated from the pressure imparting device.

In some implementations, the optical sensing system and the output unit can be adapted to sense a pulse amplitude of the arterial pulse from the movement, bending, or compression of at least one portion of the optical sensing system relative to other portions of the optical sensing system, which can result in a change in the optical signal received by the optical detector. In some implementations, the optical sensing system can be configured to detect optical signals representative of a series of arterial pulses and the output unit can be adapted to determine a pulse waveform for each of the series of arterial pulses.

In some aspects, a method of measuring a vital sign of a subject includes placing a sensor fixation device against an anatomical location of a subject, sensing movement corresponding to an arterial pulse, and generating a measure of the vital sign. The sensor fixation device holds an optical sensing system comprising an optical source, an optical refractor and an optical detector, all of which are held by the sensor fixation device and move with movement of the sensor fixation device. An arterial pulse can result in the movement, bending, or compression of at least one portion of the optical sensing system relative to other portions of the optical sensing system, which can result in a change in a optical signal received by the optical detector. The vital sign is generated using an input indicative of the changes in the amount of optical energy received by the optical detector.

In some implementations, the method can include applying a pressure to the anatomical location of the subject with the sensor fixation device. For example, the method can include reducing the pressure applied to the anatomical location with the sensor fixation device over the period of time and determining a series of pulse characteristics for arterial pulses during the period of time from changes in the optical signal received by the optical detector over the period of time. The generated measure of the vital sign can be based on the series of pulse characteristics during the period of time.

In some implementations, the method can include obtaining a measured blood pressure measurement, an initial pulse characteristic, and a subsequent pulse characteristic and generating a vital sign based on the measured blood pressure measurement, the initial pulse characteristic, and the subsequent pulse characteristic. The initial pulse characteristic can be obtained at an initial time, and a subsequent pulse characteristic can be obtained at a subsequent time, using an input indicative of the sensed movement from the optical sensing system. The measured blood pressure measurement can be obtained at a measurement time closer to the initial time than to the subsequent time.

In some implementations, the optical source and the optical refractor can be configured to produce a speckle pattern output that changes in response to relative movement of optical source and the optical refractor.

In some implementations, the vital sign can be at least one of a heart rate, an arterial pulse waveform, a systolic blood pressure, a diastolic blood pressure, a mean arterial blood pressure, a pulse pressure, and an arterial compliance.

In some implementations, generating the measure of the vital sign can include determining a pulse amplitude from changes in the amount of optical energy received by the optical detector.

In some aspects, a vital sign measurement device includes a sensor fixation device, an optical sensing system, and an output unit. The sensor fixation device is adapted to be placed against an anatomical location of a subject, within which is an artery. The optical sensing system includes an optical source device and an optical detector, both of which are held by the sensor fixation device and move with movement of the sensor fixation device. The optical source device is configured to produce a speckle pattern and the optical detector is positioned to detect at least a portion of the speckle pattern output and generate therefrom the detected portion of the speckle pattern output. The optical sensing system can sense an arterial pulse from the movement, bending, or compression of at least one portion of the optical sensing system relative to other portions of the optical sensing system, which can result in a change in the optical signal received within the detected portion of the speckle pattern output. The output unit generates a measure of the vital sign using a signal indicative of the optical signal received within the detected portion of the speckle pattern.

In some implementations, the sensor fixation device can be an inflatable cuff. In some implementations, the vital sign measurement device can include pressure sensor to detect a pressure applied to the anatomical location. In some implementations, the output unit can receive, from a pressure sensor, a pressure input indicative of the pressure applied to the anatomical location and generate a vital sign using the input from the optical sensing system and the pressure input.

In some implementations, the anatomical location of the subject is an upper arm, and the sensor fixation device is configured so that the optical sensing system is positionable to sense movement due to a pulse of a brachial artery.

In some implementations, the optical source device can include an optical source and a diffuser that diffuses an optical signal produced by the optical source to produce the speckle pattern output. For example, the diffuser can include polyoxymethylene, a white fluoropolymer, polyamide, or a combination thereof. In some implementations, the optical signal can travel through a portion of the diffuser having a thickness of between 0.2 mm and 1.0 mm.

In some implementations, the optical source device can include an optical source and a mirror with surface imperfections that refracts an optical signal produced by the optical source to produce the speckle pattern.

In some implementations, the vital sign measurement device can include a spatial optical occluder adapted to prevent the optical detector from receiving a portion of the speckle pattern output. For example, the spatial optical occluder can be a blocking structure having an optical aperture formed therein.

In some implementations, the optical detector can have an optical energy receiving portion having a smaller surface area than the area of the speckle pattern output. For example, the detected portion of the speckle pattern can be less than 100 times an area of an average speckle of the speckle pattern. In some implementations, the detected portion of the speckle pattern can be between 1 and 25 times the area of an average speckle of the speckle pattern output.

In some implementations, optical source includes a coherent light source.

In some implementations, the optical detector can include a plurality of optical detection regions, each optical detection region adapted to receive optical energy from the speckle pattern from a plurality of detected regions of the speckle pattern output. In some implementations, the optical detector can be a CCD or CMOS detector.

In some implementations, the vital sign can be at least one of a heart rate, an arterial pulse waveform, a systolic blood pressure, a diastolic blood pressure, a mean arterial blood pressure, a pulse pressure, and an arterial compliance.

In some implementations, the vital sign measurement device can include a spring attached to at least a portion of the optical sensing system to counter a force from the arterial pulse and to return the optical sensing system to an initial state after the arterial pulse. In some implementations, the vital sign measurement device can include a sensor pad held by the sensor fixation device adjacent to the anatomical location. Modulation of the sensor pad can result in relative movement, compression, or bending of portions of the optical source that can result in a modulation of the speckle pattern output.

In some implementations, the optical sensing system can be adapted to sense a pulse amplitude of the arterial pulse from the movement, bending, or compression of at least one portion of the optical sensing system relative to other portions of the optical sensing system, which can result in a series of changes in the detected portion of the speckle pattern output. In some implementations, the optical sensing system can be configured to detect optical signals representative of a series of arterial pulses and the output unit can be adapted to determine a pulse waveform for each of the series of arterial pulses In some aspects, a method of measuring a vital sign in a subject can include placing a sensor fixation device against an anatomical location of a subject, generating a speckle pattern using an optical source device held by the sensor fixation device, detecting, using an optical detector held by the sensor fixation device, a portion of the speckle pattern output and generating therefrom a signal indicative of optical energy received at the detected portion of the speckle pattern, the detected portion of the speckle pattern changing in response to an arterial pulse, and generating a measure of the vital sign using the generated signal indicative of optical energy received at the detected portion of the speckle pattern.

In some implementations, the vital sign can be at least one of a heart rate, an arterial pulse waveform, a systolic blood pressure, a diastolic blood pressure, a mean arterial blood pressure, a pulse pressure, and an arterial compliance.

In some implementations, the measure of the vital sign can include detecting a number of oscillations in optical energy received by the optical detector during an arterial pulse. In some implementations, the generation of the measure of the vital sign using the input indicative of the sensed movement can include taking the time derivative of the input indicative of the sensed movement.

In some aspects, a vital sign measurement device includes a sensor fixation device, an optical sensing system, and an output unit. The sensor fixation device is adapted to be placed against an anatomical location of a subject, within which is an artery. The optical sensing system includes an optical source, a diffuser, and an optical detector. At least one of the optical source, the diffuser, and the optical detector is held by the sensor fixation device and adapted to move in response to an arterial pulse relative to at least one of the other components of the optical sensing system. The optical source and the diffuser are configured to produce a speckle pattern. The optical detector is positioned to detect a portion of the speckle pattern output and to generate therefrom a signal indicative of optical energy received within the detected portion of the speckle pattern. The output unit generates a measure of the vital sign using the generated signal indicative of optical energy received within the detected portion of the speckle pattern.

The details of one or more embodiments of the invention are set forth in the accompanying drawings and the description below. Other features, objects, and advantages of the invention will be apparent from the description, drawings, and claims.

DESCRIPTION OF DRAWINGS

FIG. 12 depicts an electrical signal produced by an optical detector receiving a portion of a speckle pattern modulated by an arterial pulse.

Like reference symbols in the various drawings indicate like elements.

DETAILED DESCRIPTION

Figure 1:
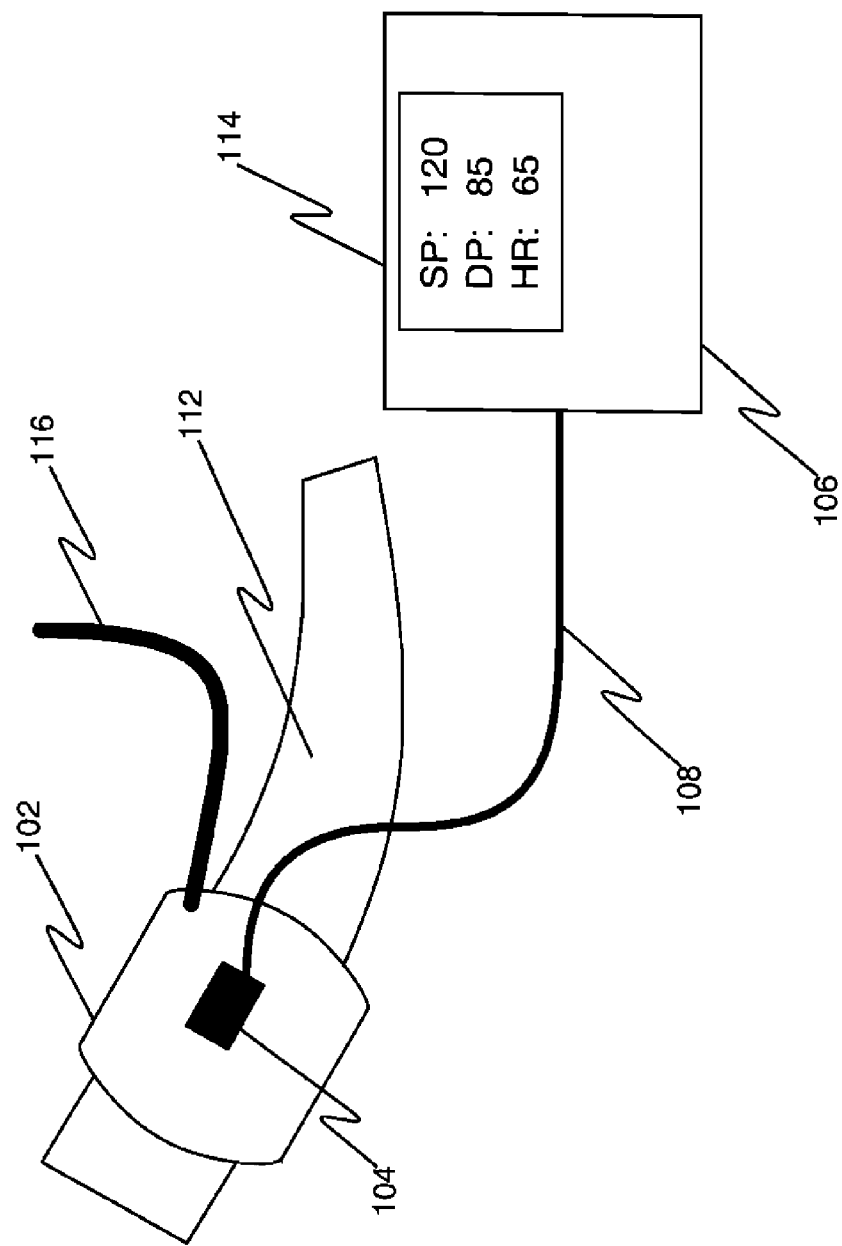
FIG. 1 depicts one implementation of the vital sign measurement device.

As shown in FIG. 1, a vital sign measurement device can include a sensor fixation device 102, an optical sensing system 104, and an output unit 106. An output from the optical sensing system 104 can be used to determine the measurement of a vital sign. The sensor fixation device 102 can be placed against an anatomical location of a subject 112, within which is an artery 118. The optical sensing system 104 can be positioned to sense movement corresponding to an arterial pulse when the sensor fixation device 102 is placed against the anatomical location of the subject 112. The optical sensing system 104 can include an optical source 202, an optical refractor 212, 214, or 216 and an optical detector 240, all of which can be held by the sensor fixation device 102 and move with movement of the sensor fixation device 102. An output unit 106 can receive input from the optical sensing system 104 that is indicative of movement corresponding to an arterial pulse and can generate a measure of a vital sign. The optical sensing system 104 can sense an arterial pulse from the movement, bending, or compression of at least one portion of the optical sensing system relative to other portions of the optical sensing system, which results in changes to the optical signal received by the optical detector.

For example, a vital sign can include a heart rate, an arterial pulse waveform, a systolic blood pressure, a diastolic blood pressure, a mean arterial blood pressure, a pulse pressure, and/or a measurement of arterial compliance. In some implementations, the vital signs can be determined from the timing of arterial pulses, the amplitude and/or magnitude of arterial pulses, or from arterial pulse waveforms. In some implementations, the vital signs can be determined from output received from the optical sensing system 104 alone or in combination with other data (e.g., data regarding the pressure within a pneumatic cuff). For example, in some implementations, a heart rate can be determined from the output received from the optical sensing system 104 alone.

Sensor Fixation Device

The sensor fixation device 102 can be any structure adapted to hold and position an optical sensing system 104 or a portion thereof adjacent to an anatomical location of a subject 112 such that the optical sensing system 104 can detect an arterial pulse. The sensor fixation device 102 can hold the optical sensing system 104 adjacent to an anatomical location of a subject 112 at a predetermined sensor fixation pressure or at an adjustable sensor fixation pressure. For example, the sensor fixation device 102 can be an adhesive bandage or a cuff (e.g., an elastic cuff or an inflatable cuff). In some implementations, the sensor fixation device 102 can be an inflatable cuff 120 having an inflatable bladder 122. The bladder 122 can be pneumatically connected to a pump 124 via a hose 116. In some implementations, the sensor fixation device 102 can apply a pressure to an anatomical location of a subject 112. For example, a pneumatically inflatable cuff can be inflated (e.g., via a pump 124) and deflated (e.g., via a valve 126) to adjust the pressure applied to a portion of a subject's body 112. In some implementations, the device can include a pressure imparting device (e.g, an inflatable cuff) adapted for placement proximal to the placement of the sensor fixation device 102, which holds the optical sensor system 104.

Figure 2A:
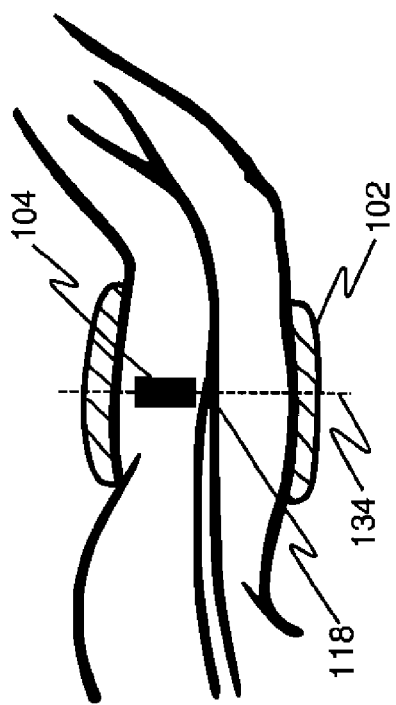
FIGS. 2A, 2B, and 2C depict various implementations of the vital sign measurement device positioned on an upper arm, and showing three different levels of cuff pressure relative to arterial systolic pressure.
Figure 2B:
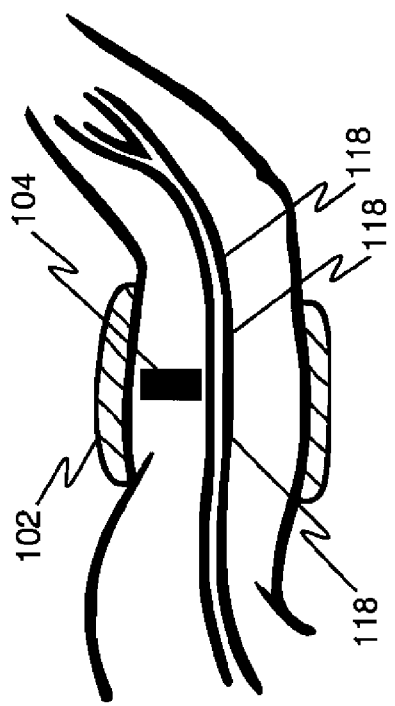
Figure 2C:
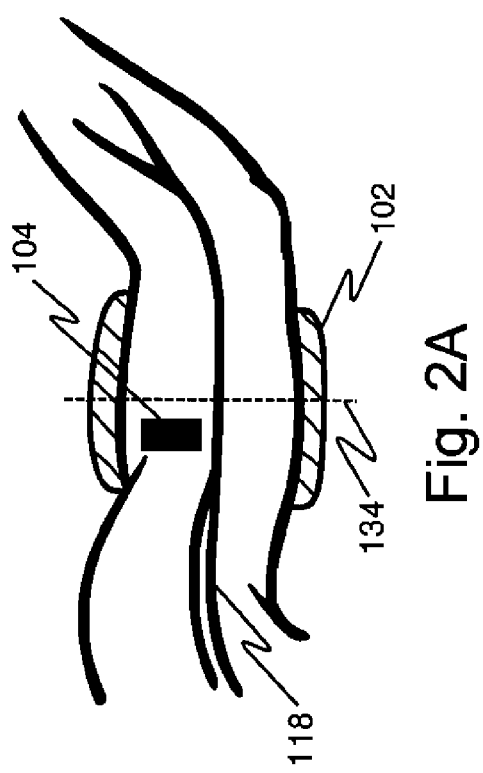

The sensor fixation device 102 can be applied to any portion of a subject's body. In some implementations, the sensor fixation device 102 is sized and arranged for placement at an anatomical location of a subject's body adjacent to a predetermined artery 118 of the subject. As shown in FIGS. 2A, 2B, and 2C, the sensor fixation device 102 can be positioned on an upper arm (above a subject's elbow) so that the optical sensing system 104 can sense movement corresponding to an arterial pulse in the brachial artery 118. The sensor fixation device 102 can also be adapted for placement on the wrist so that the optical sensing system 104 can sense movement corresponding to an arterial pulse in the radial artery. The sensor fixation device 102 can also be positioned on a leg (e.g., at the ankle to detect pulses in an artery), the neck, or any other part of the body where an arterial pulse can be detected.

As shown in FIGS. 2A, 2B, and 2C, the optical sensing system 104 can be positioned proximal to the midpoint of the sensor fixation device 102 (as shown in FIG. 2A), at the mid point of the sensor fixation device 102 (as shown in FIGS. 2B and 2C), or distal to the mid point of the sensor fixation device 102 (not shown). The placement of the optical sensing system 104 within the sensor fixation device 102 can impact the data obtained. In some implementations, a pressure applied to an artery lying below the surface of an anatomical location can be non-uniform. For example, although a body placement device 102 can apply a uniform pressure, the pressure transmitted through the layers of tissue can result in a non-uniform pressure against an artery lying some distance below the surface. In some implementations, the pressure applied to an artery lying some distance below the skin by an inflatable cuff can be greatest at the cuff midline and less at the cuff margins. The location of the optical sensor system 104 relative to the sensor fixation device 102 can be fixed to optimize the sensitivity to selected features of the arterial pulse. In some implementations, the optical sensor system 104 can be located at the midline of the cuff such that it is not responsive to pulsatile enlargement of the arterial segment under the proximal part of the cuff when the cuff pressure exceeds systolic pressure, thereby allowing a precise determination of the systolic pressure when the midsection of the arterial segment opens.

In other implementations, the optical sensor system 104 can be located near the distal margin of the cuff such that it is responsive specifically to the pulsatile arterial dimension changes at that location. Accordingly, the unique features of the arterial pulse waveform at diastolic pressure at a distal position can be identified, and effects of arterial compliance in more distal arteries can be detected. Outward flexing of the skin at the midline of the cuff, and also distal to the midline, occurs during systole when the cuff pressure is below systolic pressure. At cuff pressures exceeding systolic blood pressure, the arterial oscillations are limited to the proximal area of the cuff, as discussed above. In some implementations, the optical sensing system 104 can be located on a body fixation device 102 separate from a pressure imparting device adapted to be placed against a second anatomical location of a subject proximal to the anatomical location of the sensor fixation device 102 to allow for arterial pulse detection by the optical sensing system at a position distal to and separated from the pressure imparting device. For example, the pressure imparting device can be an inflatable cuff. In some implementations, both the pressure imparting device and the body fixation device 102 can be inflatable cuffs.

FIG. 2A depicts a sensor fixation device 102 imparting a pressure on the arm exceeding arterial systolic pressure of the brachial artery sufficient to result in a minimal arterial opening under the leading edge of the sensor fixation device 102 at systole. The amount of pressure imparted against the sensor fixation device 102 will pulsate slightly due to the arterial expansion at the leading edge during an arterial pulse. No arterial opening occurs at the positioning of the optical sensing system 104, and therefore the optical sensing system 104 does not produce a pulsatile signal. A pulsatile signal, however, will occur at a higher pressure if the optical sensing system 104 is located at a position proximal to the midpoint of the sensor fixation device 102 than if it is located at the midpoint of the sensor fixation device 102.

FIG. 2B depicts a sensor fixation device 102 imparting a pressure slightly exceeding arterial systolic pressure, such that the arterial opening 118 extends nearly to the midpoint of the sensor fixation device 102 at systole. The oscillation in pressure imparted against the sensor fixation device 102 during an arterial pulse pressure would be much larger than in the case of FIG. 2A, as the arterial expansion occurs over nearly half of the segment located within the sensor fixation device. Nevertheless, no arterial opening occurs at the sensor fixation device 102 midpoint, and therefore the optical sensing system 104 does not produce a pulsatile signal.

FIG. 2C depicts a sensor fixation device 102 imparting a pressure below arterial systolic pressure, such that the entire artery segment 118 opens momentarily at systole. The oscillations in pressure imparted against the sensor fixation device 102 during an arterial pulse will be even greater in amplitude. The arterial opening at the location under the optical sensing system causes the optical sensing system to register a pulsatile signal.

Figure 3:
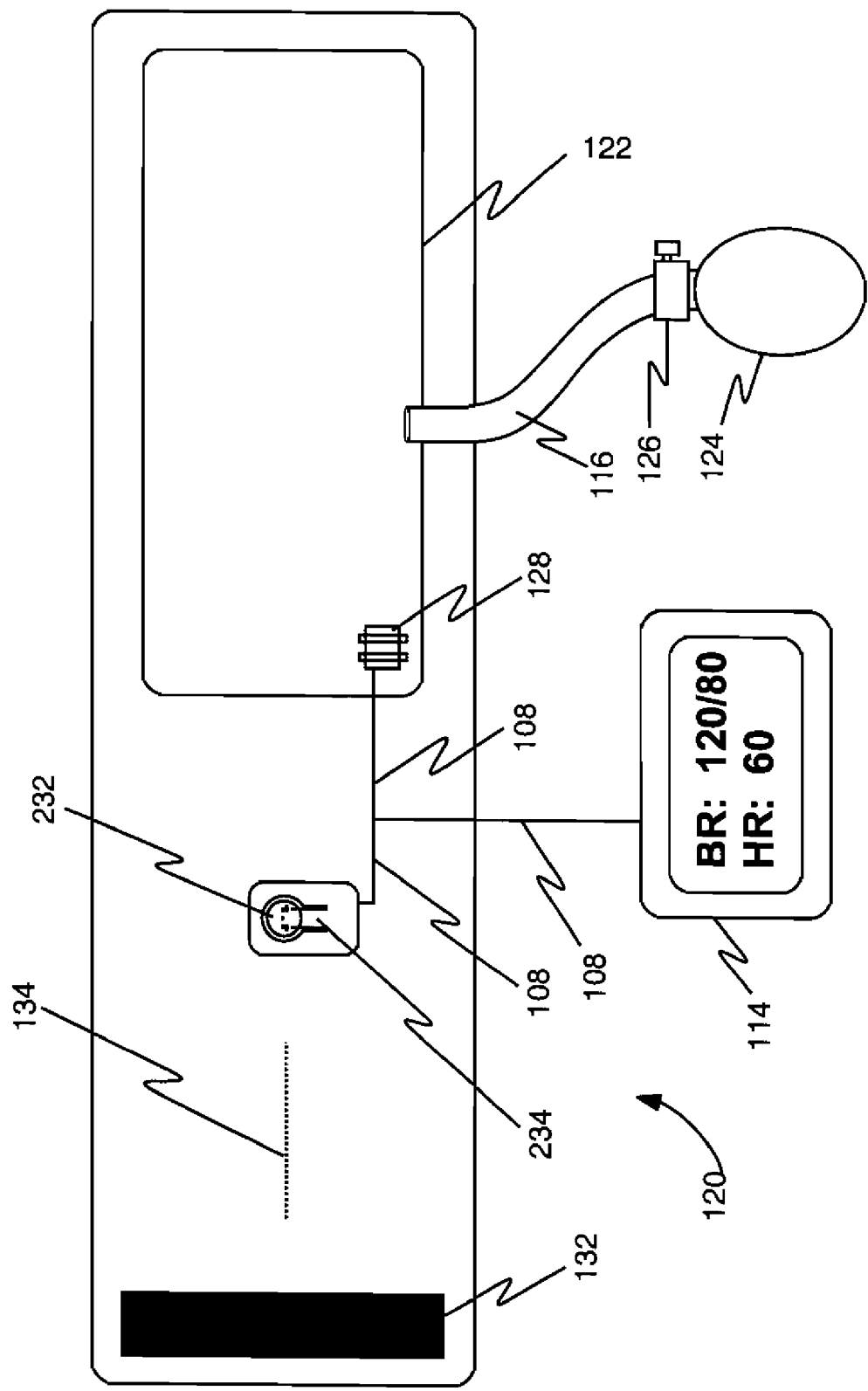
FIG. 3 depicts an implementation of a vital sign measurement device having a sensor fixation device with an inflatable bladder.

FIG. 3 depicts one implementation of a sensor fixation device 102. The sensor fixation device can be an inflatable cuff 120 having an inflatable bladder 122. The inflatable cuff 120 can be adapted to be wrapped around the upper arm of a subject to allow the optical sensing system 104 to detect arterial pulses from the brachial artery. The components of the optical sensing system 104 can be packaged within an optical sensor housing 200 located at the at the midpoint 134 of the cuff 120. The cuff 120 can include hook and loop fasteners 132 (e.g., Velcro®) or other fastening devices, which can be used to secure the cuff 120 around a limb of a subject. The cuff 120 can be wrapped around a subject's limb and the bladder 122 inflated to impart a pressure on the limb. The bladder 122 can be connected to a pump 124 by a hose 116. The bladder 122 can also be attached to a valve 126 which can control the deflation of the bladder 122. The pressure in the bladder 122 can be measured with a pressure transducer 128. The pressure transducer 128 can be located in the bladder, as shown, or can be pneumatically connected to the bladder 122 (e.g., via the hose 116).

Figure 4:
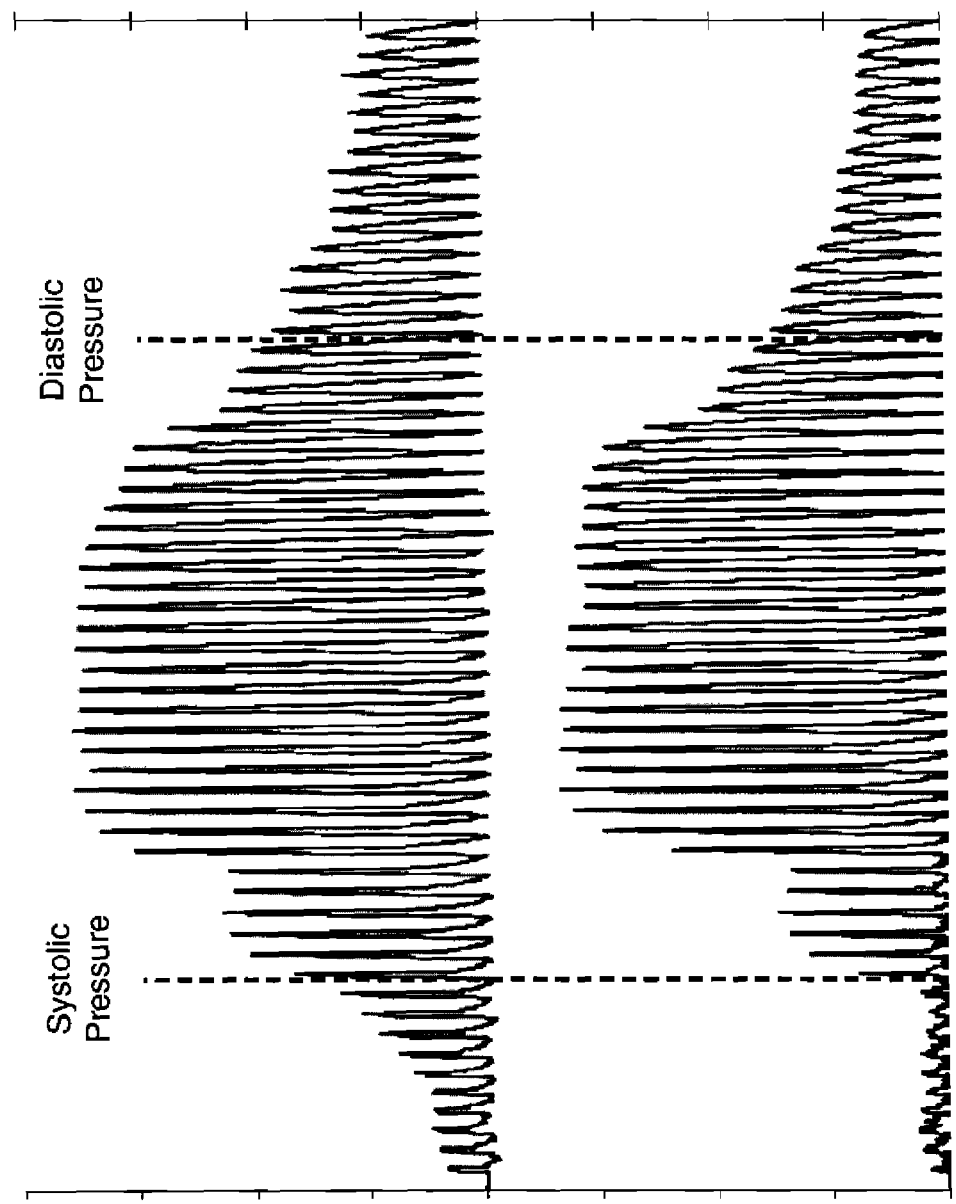
FIG. 4 depicts a series of pulses during deflation of a cuff detected by a pressure sensor pneumatically coupled to the cuff compared to simultaneously obtained pulses detected by an optical sensing system held by a sensor fixation device.

The top portion of FIG. 4 depicts pressure pulses sensed in a sensor fixation device 102 imparted by the series of arterial pulses as the imparted pressure by the sensor fixation device 102 is decreased from a pressure exceeding systolic blood pressure of a subject to a pressure below diastolic blood pressure of a subject. The bottom portion of FIG. 4 depicts pulses determined from the optical sensing system 104 at the midpoint of a sensor fixation device 102 as the pressure imparted by the sensor fixation device 102 is decreased from a pressure exceeding systolic blood pressure of a subject to a pressure below diastolic blood pressure of a subject. As shown, the optical sensing system 104 does not detect any pulses until the imparted pressure is at or below systolic blood pressure. In some implementations, this can allow for an accurate determination of systolic blood pressure.

Output Unit

Detected movements from the optical sensing system 104 can be transmitted via electrical wires 108 to a display device 114. In some implementations, as shown in FIG. 3, electrical wires 108 can connect a pressure transducer 128 to a display device 114. An output unit 106 (not shown in FIG. 3) can be part of the display unit 114, can be within the optical sensor housing 200, can be in another portion of the cuff assembly, or can be remotely located and in communication with the optical sensing system 104 via wireless transmissions. In some implementations, the output unit 106 can transmit vital sign measurements via wireless transmission. In some implementations, the optical sensing system 104 can transmit data regarding the amount of light received by a optical detector to an output unit 106 via wireless transmission. The output unit 106 can comprise a processor to determine the vital sign from signals from the optical sensing system 104 with or without other data. In some implementations, as shown in FIG. 1, the output unit can include a display to depict the vital sign. In some implementations, the output unit can include an alarm system to produce a human detectable signal when a vital sign measurement generated by the output unit meets a predetermined criteria. For example, the output unit can be adapted to create a visual or audio alarm to alert a user that a detected vital sign is outside of a predetermined range. The output unit 106 can perform a number of data processing steps, calculations, or estimating functions, some of which are discussed below.

Optical Sensing System

The optical sensing system 104 can include an optical source 202, an optical refractor 212, 214, or 216 and an optical detector 240, all of which can be held by the sensor fixation device 102 and move with movement of the sensor fixation device 102. In some implementations, the optical sensing system 104 can act as a motion sensing system (e.g., a motion sensing system adapted to detect localized motion associated with an arterial pulse). The optical sensing system 104 can detect motion corresponding to an arterial pulse when the sensor fixation device is placed against the anatomical location of the subject. As shown in FIGS. 5A, 5B, 5C, 6A, 6B, and 6C, an optical sensing system 104 can be contained within an optical sensor housing 200.

In some implementations, the optical sensing system 104 can include an optical source 202 optically coupled to an optical refractor 212, 214, or 216, such that light waves travel from the optical source 202 to the optical refractor 212, 214, or 216. The optical source 202 can be a coherent light source, for example a laser. In some implementations, an LED can be used as the optical source 202.

In some implementations, the optical refractor can be an optical waveguide 212, a diffuser 214, a mirror with surface imperfections 216, or another refractive material. The movement, bending, or compression of the optical refractor 212, 214, or 216 can alter the path taken by optical waves 218 traveling through the optical waveguide 212, through the diffuser 214, or refracting off of the mirror 216, thus causing the amount of optical energy (e.g., light) received by the optical detector 240 or 242 to change. Likewise, the movement of the optical source 202 or the optical detector 240 or 242 can result in changes to the amount of optical energy (e.g., light) received by the optical detector 240 or 242. By monitoring the changes in the amount of received optical energy, an arterial pulse can be characterized, which can be used to determine a vital sign. For example, the amplitude of the pulse can be determined, or the waveform shape of the pulse can be determined.

In some implementations, the optical detector 240 or 242 can be a PIN diode photodetector, a CCD (Charge-Coupled Device) detector, or a CMOS (Complementary Metal-Oxide-Semiconductor) detector. In some implementations, the optical sensing system 104 can include one or more optical detectors 240 or 242. For example, in some implementations, a series of optical detectors can each receive optical energy refracted by the optical refractor 212, 214, or 216. In some implementations, an optical detector 242 can include a plurality of optical detection regions. For example, CCD and CMOS detectors can be configured to allow for the detection of the amount of optical energy received by a plurality of discrete detection regions or can be configured to output a signal indicating the total amount of optical energy received by the CCD or CMOS detector.

In some implementations, such as those discussed below, the optical source 202 and the optical refractor 212, 214, or 216 are arranged to produce a speckle pattern. In some implementations, the compression and/or bending of a compressible or flexible optical waveguide can result in a change in the total amount of light exiting the optical waveguide or a change in a speckle pattern.

Figure 5A:
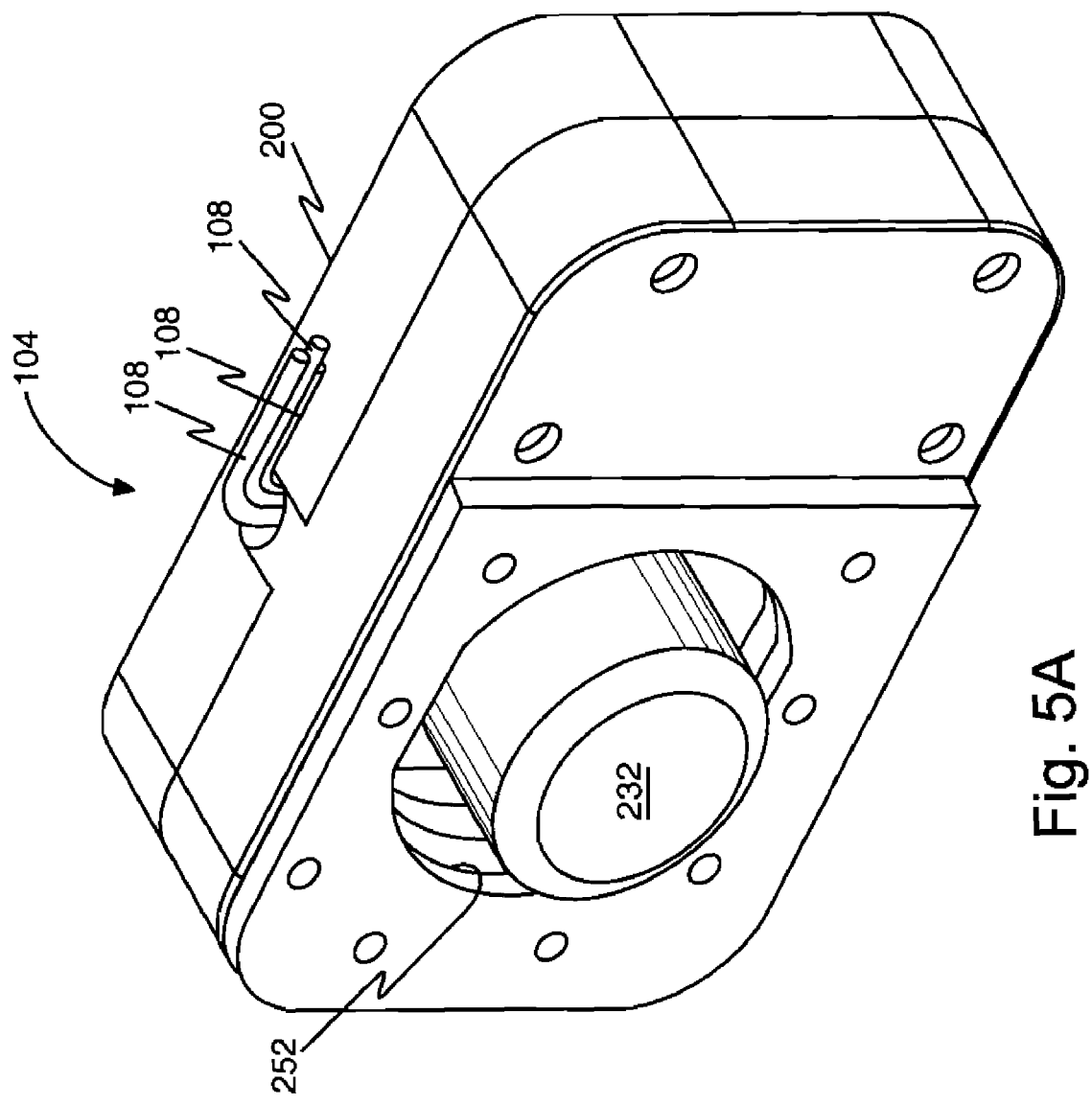
FIGS. 5A, 5B, and 5C depict an implementation of an optical sensor housing containing the components of an optical sensing system.
Figure 5B:
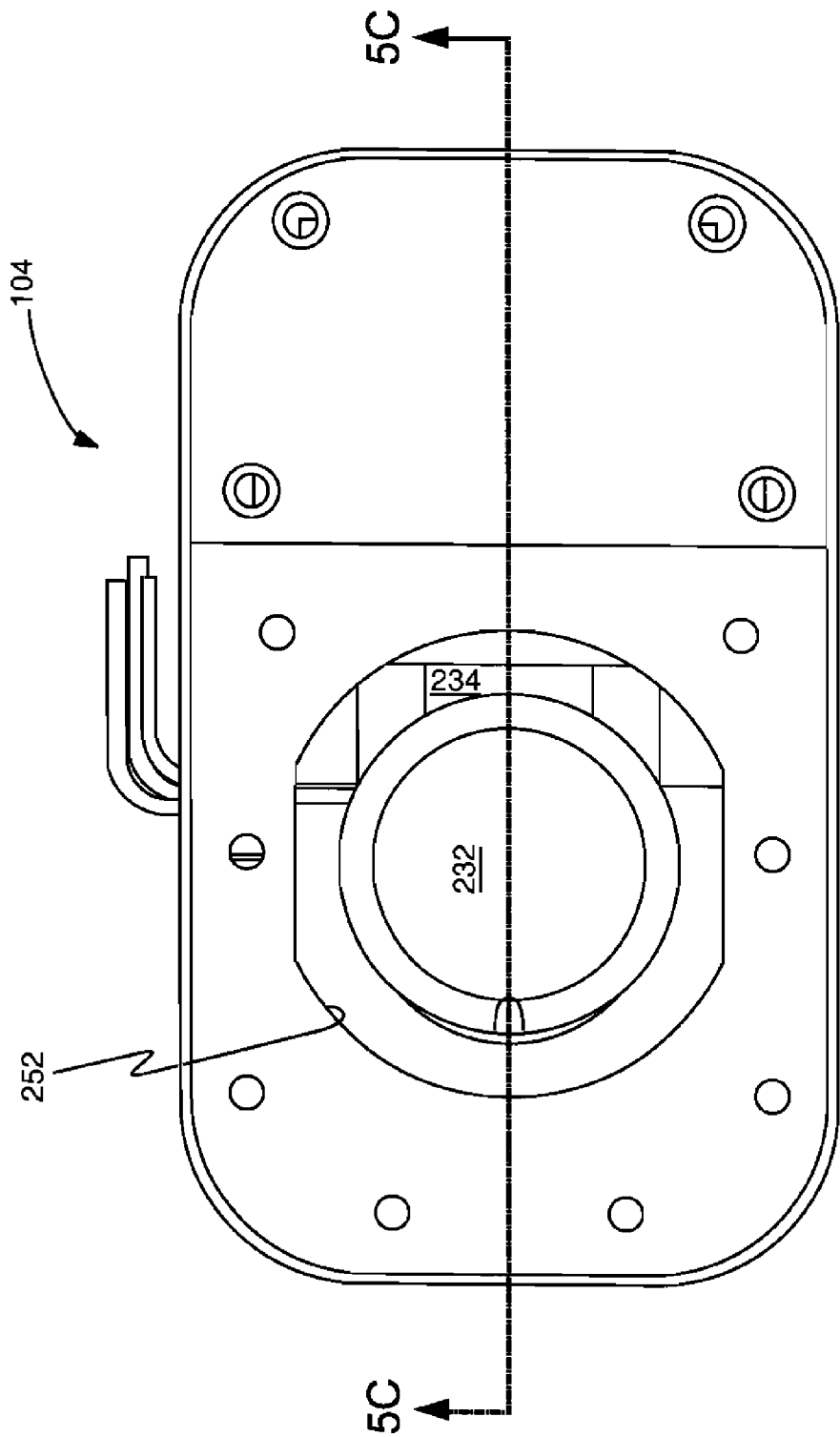
Figure 5C:
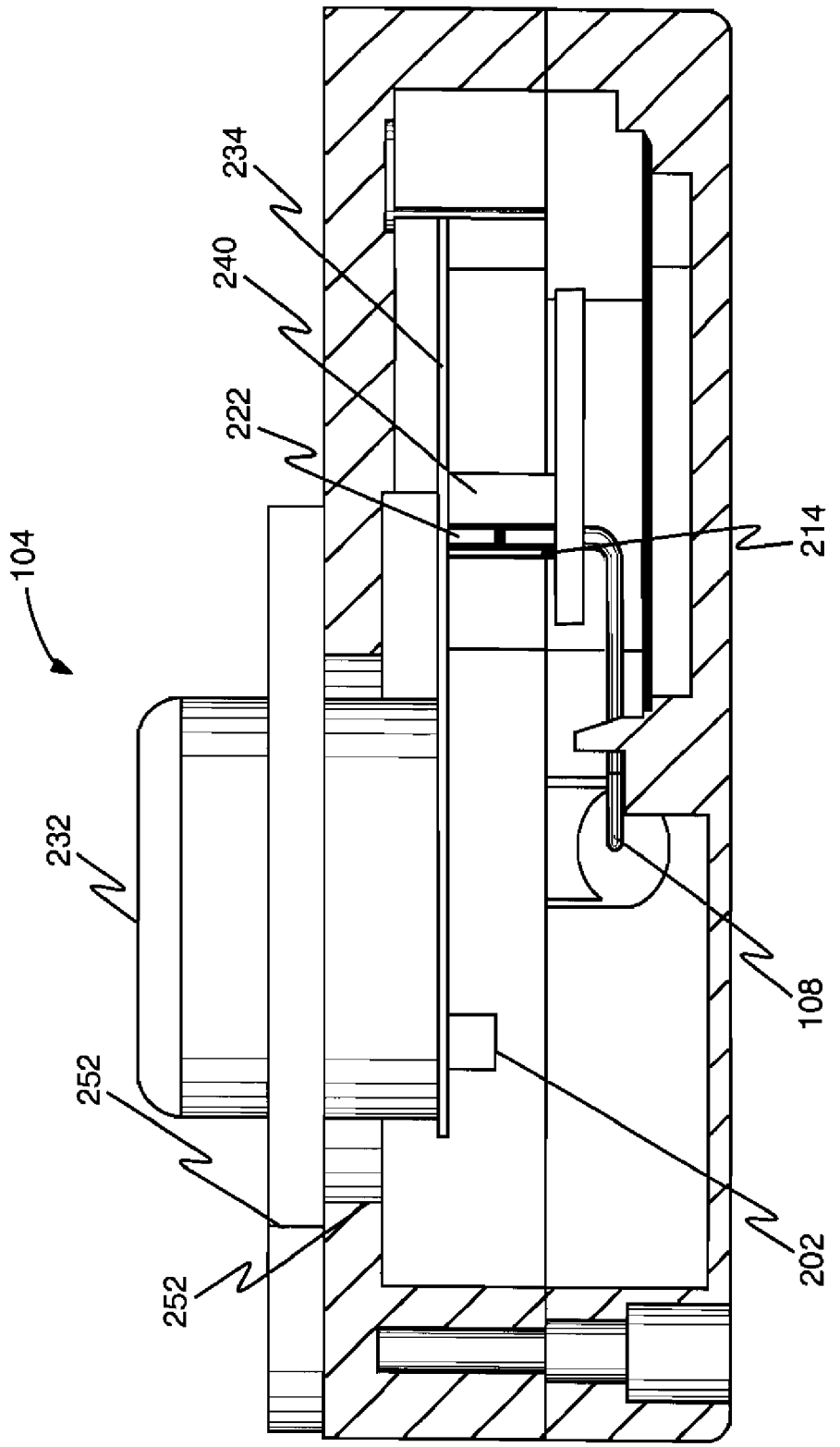

FIGS. 5A, 5B, 5C, 6A, 6B, and 6C show examples of miniaturized optical sensor housings that can be placed against a subject's skin to sense arterial pulses. The optical sensor housing 200, as shown, includes a sensor pad 232, a spring 234 attached to the sensor pad 232, a optical source 202, an optical refractor 212, 214, or 216, a optical detector 240 or 242, and wires 108 from the optical detector 240. In some implementations, the optical sensor housing 200 can also include additional elements, such as a spatial optical occluder 222 (e.g., a pin hole aperture) between the optical refractor 212, 214, or 216 and the optical detector 240 or 242, as depicted in FIG. 5C. In some implementations, the sensor housing 200 can have a width of between 0.7 and 1.3 inches (e.g., about 1 inch), a length of between 1.5 and 2.2 inches (e.g., about 1.7 inches), and a thickness of between 0.3 and 0.9 inches (e.g., about 0.6 inches).

Figure 6A:
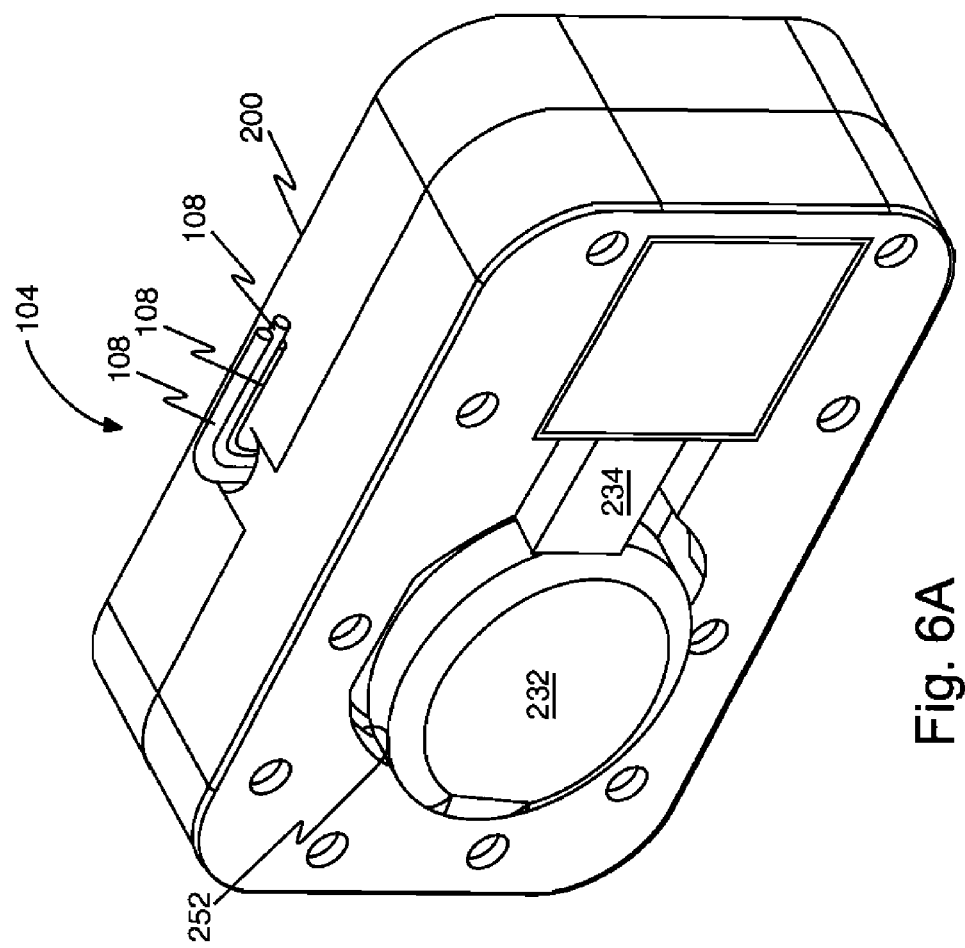
FIGS. 6A, 6B, and 6C depict an implementation of an optical sensor housing containing the components of an optical sensing system.
Figure 6B:
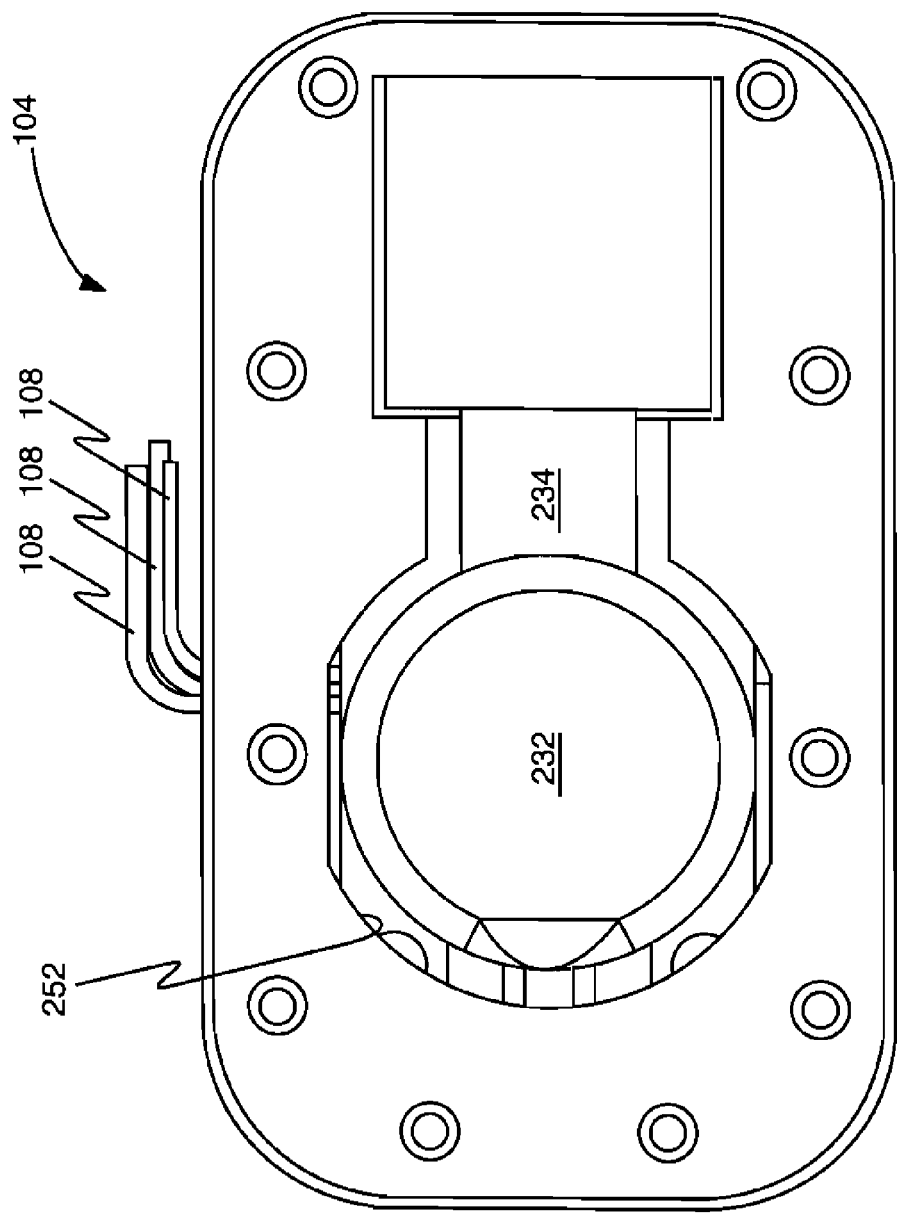
Figure 6C:
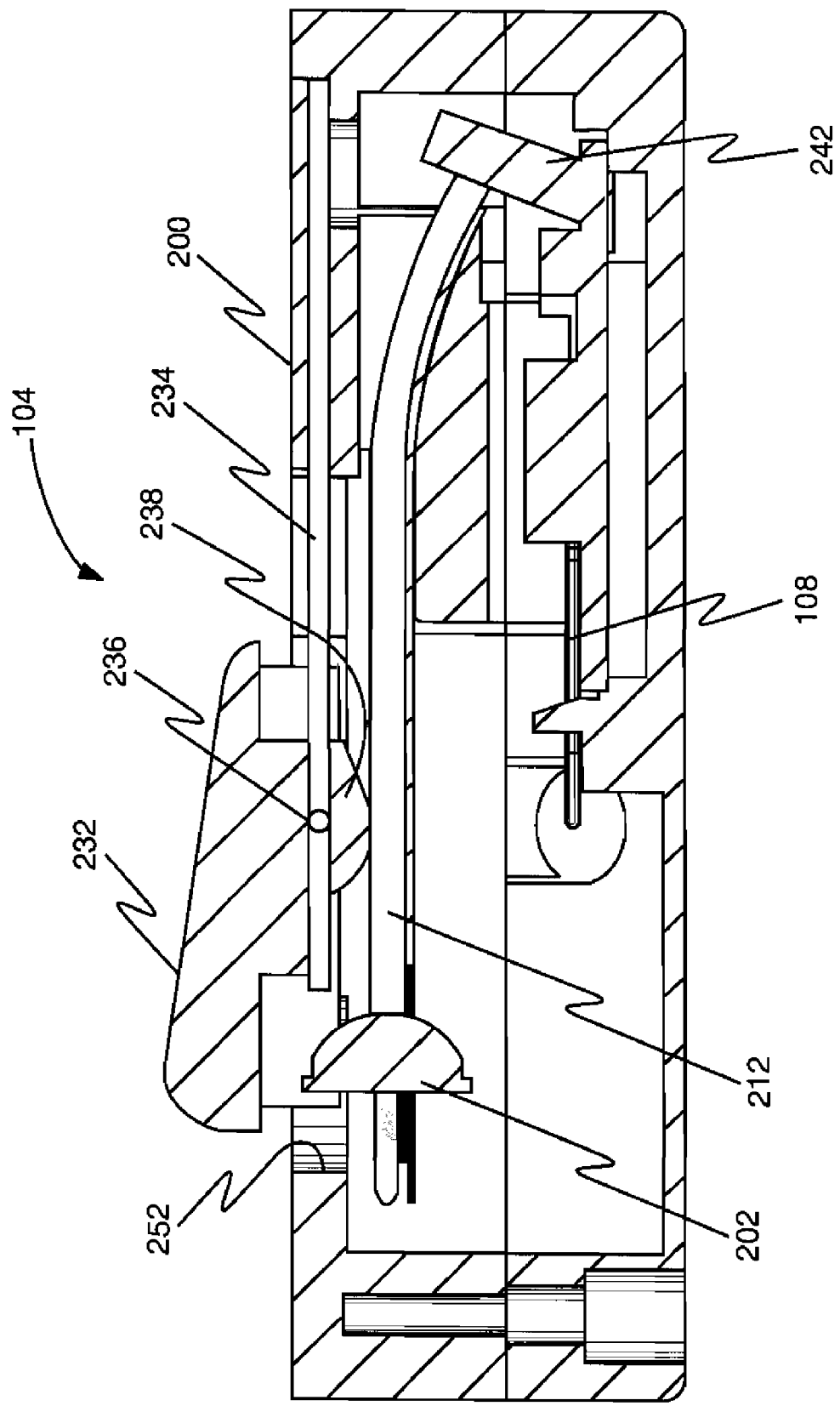

As shown in FIGS. 5A, 5B, 5C, 6A, 6B, and 6C, a sensor pad 232 adapted for placement against an anatomical location of a subject can be attached to a spring 234. The sensor pad 232 can extend out of the optical sensor housing 200 when in a relaxed state. For example, the sensor pad 232 can extend out of the optical sensor housing 200 by at least 0.1 inch (e.g., between 0.1 and 0.3 inches). As shown, the sensor pad 232 extends out from the sensor housing 200 by 0.161 inches. The sensor pad 232 can have any shape. The sensor pad 232 can have a diameter of at least 0.3 inches, for example between 0.3 and 0.8 inches (e.g., about 0.6 inches). In some implementations, for example as shown in FIG. 6C, the sensor pad 232 can be attached to the spring 234 by a hinge 236 that allows for the back and forth motion of the sensor pad 232. In some implementations, as shown in FIG. 6C, the sensor pad 232 can have an inclined upper surface.

The sensor pad 232 can be attached to or otherwise positioned to cause the relative movement of the optical source 202, the optical refractor 212, 214, or 216, any spatial optical occluder 222 if used, the optical detector 240, or a combination thereof. As shown in FIG. 6C, the sensor pad 232 can include a pressing portion 238 adapted to cause the bending, compression, or movement of an optical waveguide 212. In some embodiments, such as shown in FIG. 5C, the spring 234 can be attached to an optical source 202, such that the modulation of the spring 234 causes the movement of the optical source 202 while the optical refractor 214 remains stationary. The spring 234 can have a length of at least 0.6 inches, for example between 0.6 inches and 1.8 inches (e.g., 1.1 inches).

Various other configurations can allow for the modulation of the spring 234 to result in the relative movement of the optical source 202 and the optical refractor 212, 214, or 216.

The sensor pad 232 can also be positioned within a cutout 252. The spacing between the cutout 252 and the sensor pad 232 can impact the amount of movement of the sensor pad 232 allowed by the sensor housing 200 due to arterial pulses. The spacing between the cutout 252 and the sensor pad 232 can be about 0.1 inches.

Wires 108 can transmit data from the optical detector 240 or 242 to an output unit 106, as discussed above. In some implementations, the output unit can be included within the optical sensor housing 200 and wires 108 can transmit vital sign data to devices outside of the housing 200. In some implementations (not shown), the optical sensing system 104 can transmit data from a housing 200 by wireless transmission.

Speckle Pattern

FIGS. 7A, 7B, 8A, and 8B depict the basic principle of speckle pattern modulation. A optical source 202 can be optically coupled to an optical refractor 212, 214, or 216, such that optical waves 218 travels from the optical source 202 to the optical refractor 212, 214, or 216. The optical source 202 can provide coherent light. The optical source 202, such as a laser, can be used to illuminate the optical refractor 212, 214, or 216 to create a "speckle pattern" 260, so-called because the optical effect is the appearance of speckles 262 in the far field illumination. For example, the optical refractor can be optical waveguide 212, a diffuser 214, a mirror with surface imperfections 216 (e.g., as shown in FIGS. 9C and 10C), or another refractive material capable of forming a speckle pattern 260. The refraction can cause spatial variations in the transmitted optical waves 218 which appear as regions of darkness in a background of light. These dark regions, or speckles 262, can be of characteristic, but random, shape and size, determined by the refractive characteristics of the optical refractor 212, 214, or 216. The optical waves 218 (only a few of which are illustrated) illuminating the optical refractor 212, 214, or 216 can constructively interfere to form a speckle pattern 260 of a series of speckles 262. The relative movement, bending, or compression of the optical refractor 212, 214, or 216 relative to the optical source 202 alters the path taken by the optical waves 218 traveling through the optical refractor 212 or 210 or refracting off of the refractor 310, thus causing the speckle pattern 260 to change. For example, as an optical refractor 212, 214, or 216 is moved relative to the optical source 202, the speckle pattern 260 can seem to twinkle or, in some cases, can seem to rotate. Although the total light traveling through the optical refractor 212 or 210 or refracting off of the mirror 216 can remain relatively constant, by monitoring a select detected portion, e.g., 264, of the speckle pattern, changes in the amount of optical energy (e.g., light) in a detected portion 264 if the speckle pattern 260 can be observed. By monitoring the changes in the amount of light in the detected portion, e.g., 264, the amount of and/or speed of relative movement, bending, or compression can be determined.

Figure 9A:
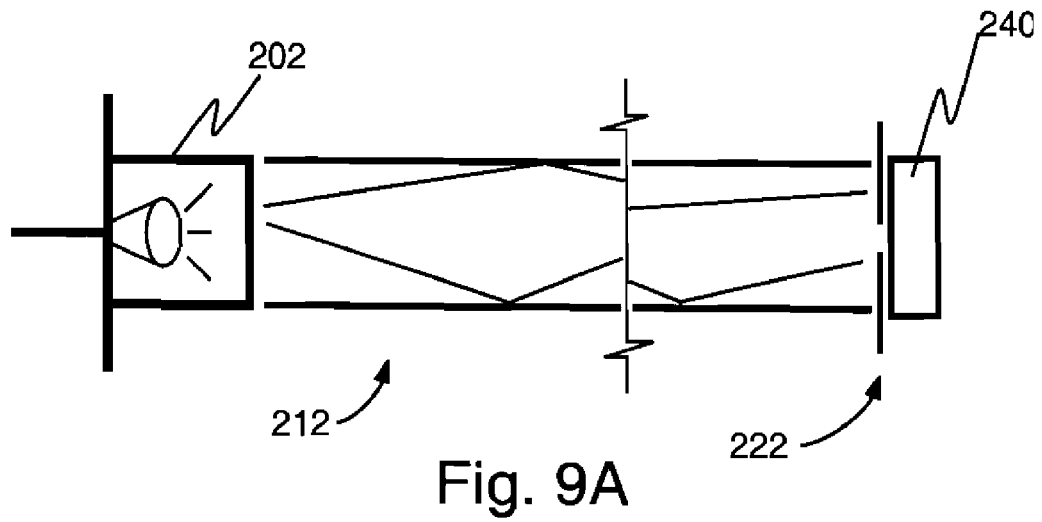
FIGS. 9A, 9B, and 9C depict implementations of the optical sensing system including a spatial optical occluder.
Figure 9B:
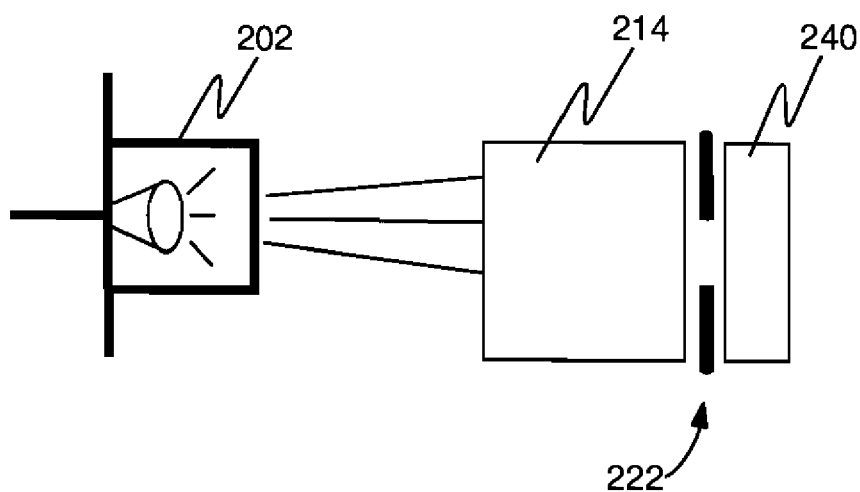

The detected portion, e.g., 264, can be limited by restricting the portion of the formed speckle pattern 260 allowed to be received by the optical detector 240 or 242. Restricting the portion of the speckle pattern 260 received by a optical detector 240 can be achieved in a number of ways. For example, as shown in FIGS. 9A, 9B, and 9C, a spatial optical occluder 222, such as a blocking structure having an optical aperture formed therein (e.g., a pin hole aperture), can be positioned between the optical refractor 212, 214, or 216 and an optical detector 240. In some implementations, the detected portion 264 of the speckle pattern 260 can be restricted by using an optical detector 240 having a smaller optical energy receiving area than the area of produced speckle pattern 260. The optical detector 240 or 242, and any intermediate spatial optical occluder 222 used, can be placed adjacent to the optical refractor 212 or 214 to ensure that the optical detector 240 or 242 only receives light from speckles within a predetermined detected portion, e.g., 264. When using a mirror with surface imperfections 216 as the optical refractor, the spacing of the optical detector 240 and any intermediate spatial optical occluder used, will determine the size of the detected portion 264 and of the produced speckle pattern 260.

The optical source 202 can be a coherent light source, for example a laser.

The optical refractor can be an optical waveguide 212, a diffuser 214, or a mirror having surface imperfections 216, or another refractive material capable of forming a speckle pattern 260. In some implementations, a device can use a combination of multiple and/or different optical elements. For example, an optical waveguide 212 can by used to guide light waves 218 to a diffuser 214.

An optical waveguide 212 can be an optical fiber or any liquid, gel, or solid that transmits light waves by internal reflection or refraction. In some implementations, the optical waveguide 212 can transmit almost 100% of the light by providing almost total internal refraction. For example, an optical waveguide 212 can include an optical material with relatively high index of refraction ($n_h$), surrounded by a material with lower index of refraction ($n_l$). In such optical waveguides 212, light is lost only when the light wave reaches the interface between the two materials at an angle less than the critical angle ($\theta_c$). The critical angle ($\theta_c$) can be calculated by the following equation.

$$\theta_c = \arc\sin(n_l/n_h)$$

In some implementations, the surrounding material with a lower refractive index can be air. In some implementations, waveguides can also be in the form of a hollow tube with a highly reflective inner surface. The inner surfaces can be polished metal.

Figure 7A:
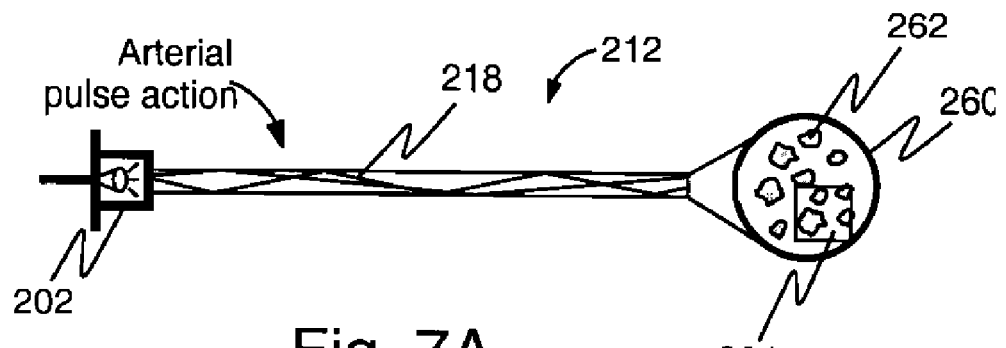
FIGS. 7A and 7B depict a speckle pattern produced by an optical source device including an optical source and a waveguide.
Figure 7B:
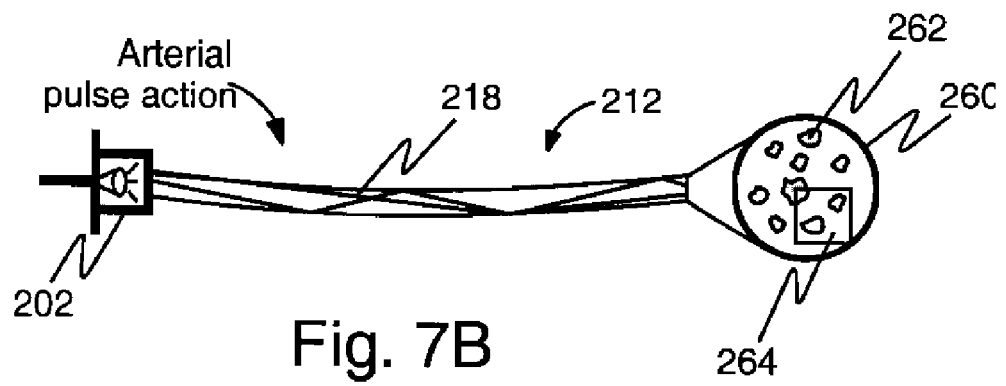

In some implementations, such as that shown in FIGS. 7A and 7B, an optical waveguide 212 causes the internal reflection of optical waves 218 within the core of the optical waveguide 212. As the optical waveguide 212 is moved or bent, the path for each light wave 115 is altered, resulting in changes in a resulting speckle pattern. In some implementations, the optical waveguide 212 can be a flexible waveguide. In some implementations, the optical waveguide 212 can be a compressible waveguide.

A diffuser 214 can be any device comprised of refractive material that diffuses, spreads out, or scatters light in some manner, such as any semitransparent liquids, gels, or solids; airborne particles; or and skin or other tissue. For example, a diffuser 214 can include polyoxymethylene (POM) (e.g., Delrin® acetal resin), white fluoropolymer (e.g., Teflon® fluoropolymer), Polyamide (PA) (Nylon®), or ground or grayed glass. In some implementations, the diffuser material can have low optical absorption at the laser wavelength, and can have refractive properties that produce sufficient light scattering over a short path length to insure that a speckle pattern is generated on the surface opposite the laser with suitable speckle size and uniformity For example, the diffuser can include a piece of polyoxymethylene (Delrin® acetal resin) having a thickness of between 0.2 mm and 1 mm (e.g., between 0.4 and 0.6 mm), such that the optical intensity is not overly diminished on the exit side but sufficiently thick to effect the requisite light scattering needed to create the speckle pattern 260.

Figure 8A:
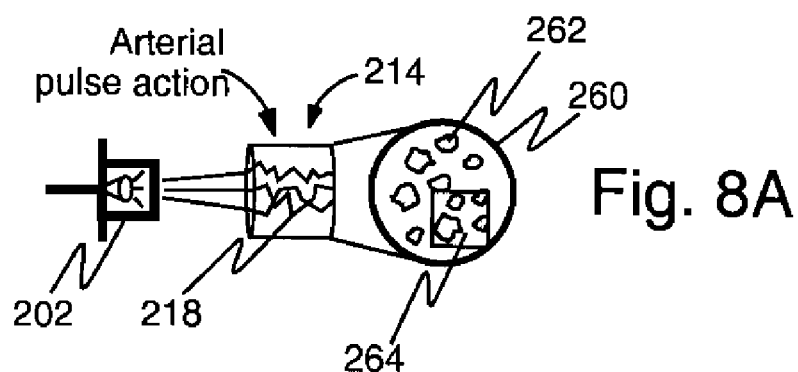
FIGS. 8A and 8B depict a speckle pattern produced by an optical source device including an optical source and a diffuser.
Figure 8B:
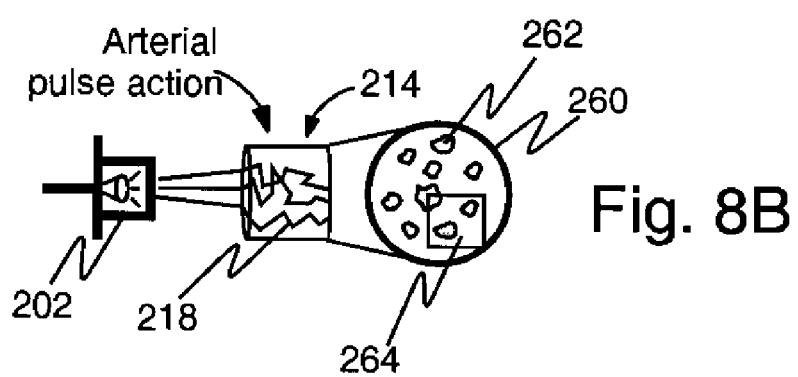
Figure 9C:
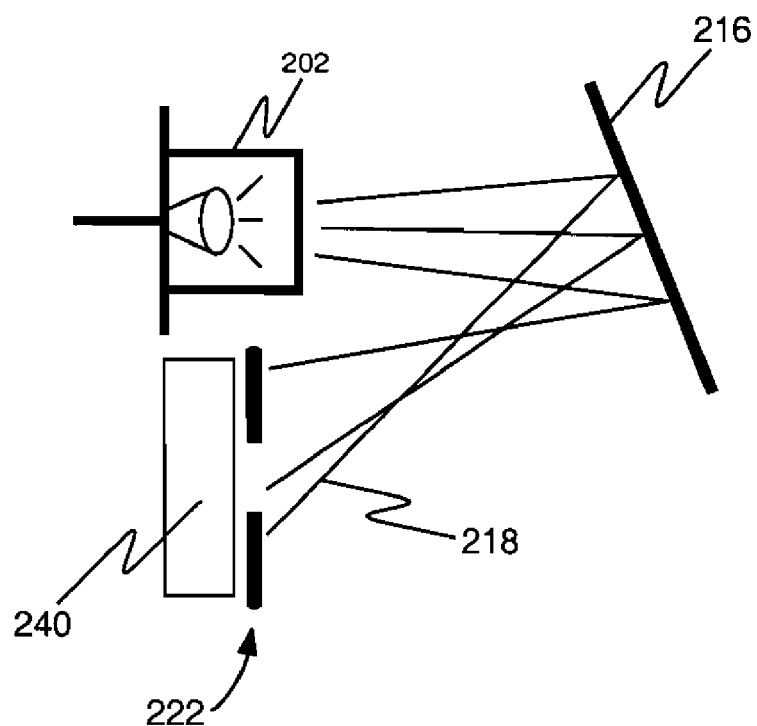

In some implementations, such as that shown in FIGS. 8A and 8B, a diffuser 214 causes the refraction of light waves within the body of the diffuser 214. The refraction of light waves within the diffuser can be caused by variations in refractive index within the diffuser 214 which result in random photon scattering. As the diffuser 214 is moved, the areas of the diffuser which cause the refraction of the light waves are also moved causing the optical waves 218 to refract differently within the diffuser 214, resulting in changes in a resulting speckle pattern 260.

In some implementation, such as shown in FIGS. 9C and 10C, the optical element can also be a mirror with surface imperfections 216. The imperfections in the mirror can result in light waves impacting the imperfections to reflect at different angles. The reflection of light off of the mirror with imperfections 216 also can result in an optical pattern 260. The relative movement of the mirror 216 in respect to the optical source 202 similarly results in changes to the optical pattern 260.

Figure 11B:
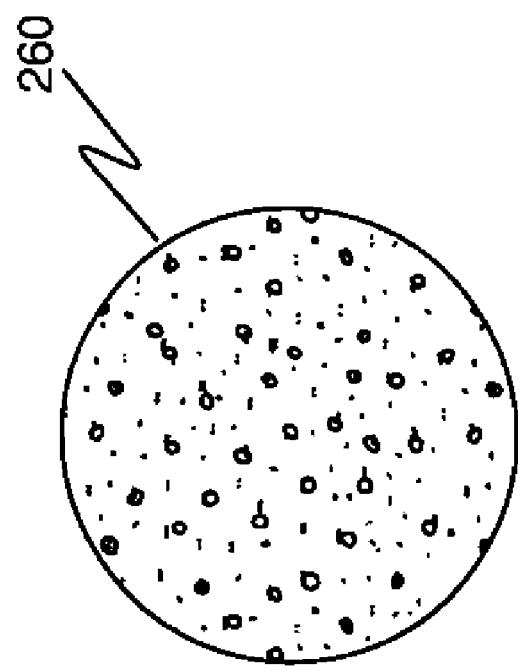
FIGS. 11A, 11B, and 11C depict speckle patterns produced by various implementations of vital sign measurement device.
Figure 11A:
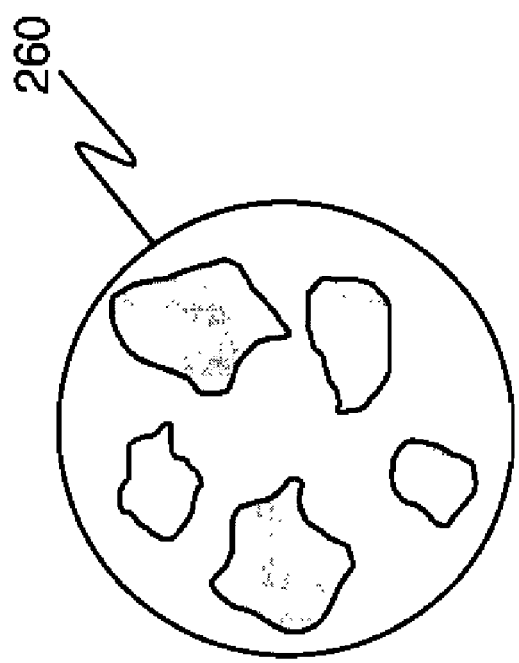

In some implementations, the characteristic size and number of individual speckles 262 can be controlled. For example, the characteristic size and number of individual speckles 262 can be controlled with an optical waveguide 212 having optimal diameter and refractive characteristics for the desired speckle 125 features. Illustrated in FIGS. 11A and 11B are the speckle patterns 260 from a laser 202 whose beam is passed through different optical fibers. In FIG. 11A, a speckle pattern with relatively few, large speckles 262 is shown, which is formed from an optical waveguide 212 having a small diameter and small index of refraction gradient. In contrast, the speckle pattern 260 shown in FIG. 1B with relatively many, small speckles 262 is formed with an optical waveguide 212 that permits much more optical interference because of a larger diameter and larger index of refraction gradient, resulting in a speckle pattern 260 with relatively many, small speckles 262.

Figure 11C:
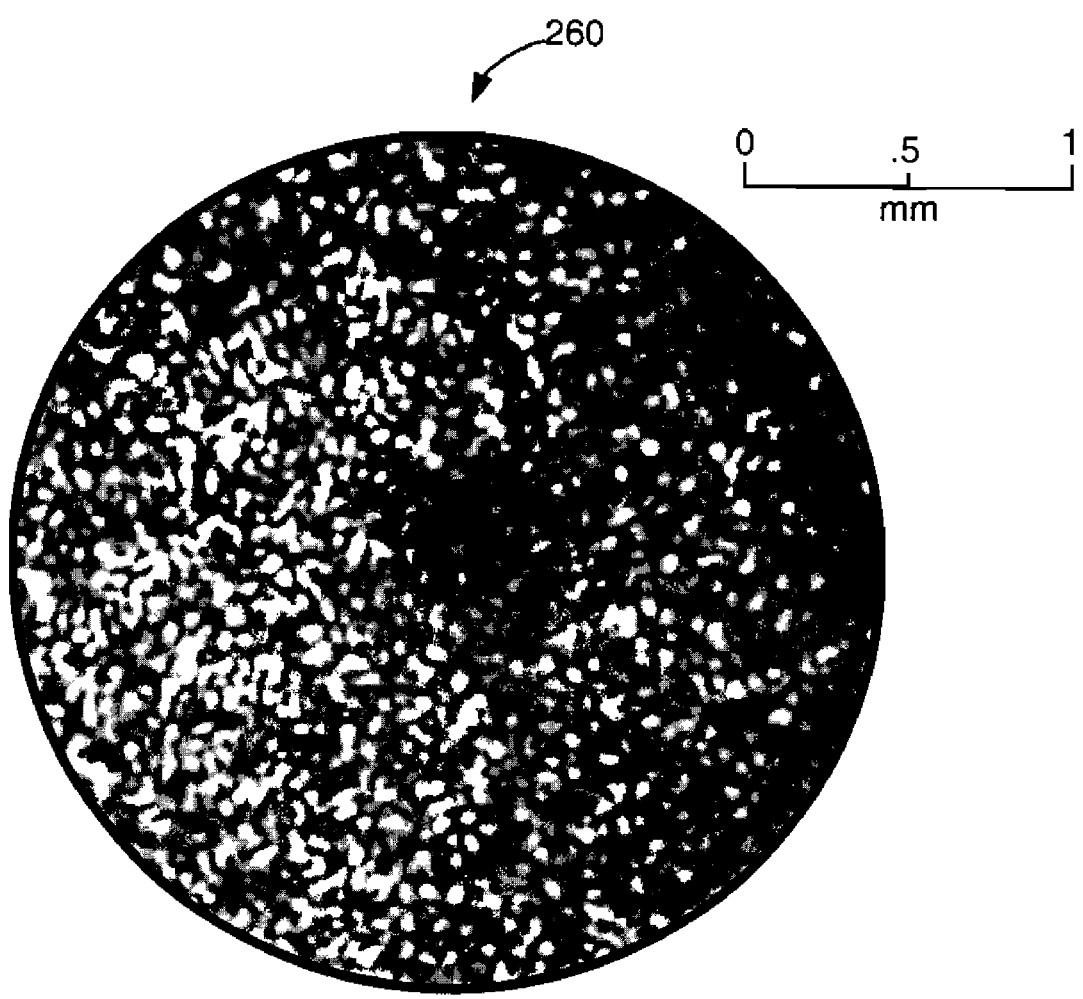

Similarly, FIG. 11C is a magnification of a speckle pattern 260 formed by passing coherent light through a diffuser 214. The bar in the upper right side of the figure indicates the size of the magnification.

In some implementations, the average speckle size of the sampled portion of a speckle pattern 260 can be at least 10 microns (for example, between 25 and 100 microns).

Sensitivity to the relative movement, bending, or compression of the optical source and the optical refractor 212, 214, or 216 can be optimized by properly sizing the detected portion 264 and fixing the separation of the optical refractor 212, 214, or 216, the optical detector 240, and any intervening spatial optical occluder 222 if used. The detected portion 264 can be sized in relation to the average speckle size so as to optimize the amplitude of fluctuations in the electrical output of the optical detector 240, which correspond to the modulation of the speckle pattern 260 that is caused by relative movement, bending, or compression of the optical refractor 212, 214, or 216, the optical source 202, or the optical detector 240 or 242. For example, by sizing an aperture of a spatial optical occluder 222 to collect only a small number of speckles, such as less than one percent of the speckle pattern 260 area, and employing suitable signal processing to the time-varying optical detector output, the time derivative of the pulse signal can be measured to allow a calculation of a vital sign. In some implementations, the optical energy receiving portion of the optical detector 240 can also have a smaller area than the area of the produced speckle pattern 260.

In some implementations, the detected portion 264 of the speckle pattern 260 can be less than one hundred times the average speckle size, for example, between 1 and 25 times the average speckle size. In some implementations, the optical detector 240 can receive up to an average of 50 speckles, for example between 1 and 5 speckles. For example, a pin hole aperture having a 125 micron diameter can be used to restrict the detected portion 264 of the speckle pattern 260 received by a optical detector 240 or 242.

Analytical Methods

The optical detector 240 or 242 of an optical sensing system 104 can generate an electrical signal 420 indicating the amount of light received. The electrical signal 420 can be a function of time. The electrical optical detector signal 420 is analyzed to determine the rate of modulation of the speckle pattern 260. For example, FIG. 12 depicts a possible electrical signal 420 indicating the modulation in an amount of optical energy received by an optical detector 240 or 242. As shown in FIG. 12, the amount of light received by the optical detector 240 can oscillate. The oscillation frequency of optical energy received by the optical detector 240 or 242 can be generally understood as the inverse of the amount of time in which a characteristic change occurs in the number or brightness of speckles within the predetermined detected portion, e.g., 264, which is received by the optical detector 240 or 242. A characteristic change occurring in the number of brightness of speckles can be generally scaled to represent a characteristic relative movement, bending, or compression of the optical source and the optical refractor. By monitoring the rate of oscillation of the amount of light received by the optical detector 240, the amplitude and/or magnitude of an arterial pulse can be determined.

In some implementations, the average amount of light received by the optical detector 240 can vary over time in response to the positioning of the light source relative to the optical refractor 212, 214, or 216 and the amount of light received by the optical detector 240 can oscillate about that average amount of light received due to the relative movement of the optical source and the optical refractor.

In some implementations, this low frequency variation in the amount of light received can be filtered out of the received signal. In some implementations, high frequency "noise" can also be filtered out. In some implementations, high and/or low frequency variations in the amount of light received by an optical detector can be filtered out of the signal from an optical detector 240 or 242 prior to determining a vital sign from the data. In some implementations, the filtering of the signal can be performed by an optical waveform prefilter 432.

The output unit 106 can determine the amplitude and/or magnitude of each arterial pulse to determine one or more vital signs. In some implementations, the amplitudes and/or magnitudes for a series of arterial pulses can be determined to determine one or more vital signs. For example, to determine the amplitude and/or magnitude of an arterial pulse from the oscillations of the amount of light received by the optical detector 240, a differentiating electrical circuit can be applied to an optical detector 240 output to produce a signal proportional to its time derivative, dE/dt. This time-derivative signal can increase in proportion to the frequency content of the optical detector electrical signal, which is proportional to the rate of modulation of the speckle pattern. Each arterial pulse (corresponding to a cardiac cycle), can, for example, characteristically exhibit a pressure increase, followed by a pressure decrease, and then a quiescent period before the start of the next pulse. The pressure increase can cause the optical source 202 to move or the optical refractor 212, 214, or 216 to move, bend, or compress such that the speckle pattern 260 modulates, the modulation rate will increase at the start of the pulse and decrease to zero at the time of maximum pulse pressure (i.e., where the pulse wave stops rising, and is about to begin its decline). As the pressure decreases, an opposite movement of the waveguide will occur, again modulating the speckle pattern such that its modulation rate increases after the maximum pulse pressure and decreases to zero when the arterial pulse has ended. FIG. 12 depicts an example of a optical detector electrical signal created by an arterial pulse. The signal dE/dt will therefore start at zero, then increase to a maximum, then decrease to zero, then increase again, and finally decrease to zero, all during the course of one arterial pulse. The pulse amplitude can be, as a first approximation, proportional to the maximum speckle pattern modulation rate, which in turn can be calculated from the maximum value of dE/dt, based on the relationship between a sinusoidal function and its derivative, i.e.:

$$dE/dt = d/dt[\sin(\omega t)] = \omega \cdot \cos(\omega t),$$

whose maximum amplitude is proportional to the maximum modulation rate during the arterial pulse cycle, or $\omega_{max}$.

The signal dE/dt can be analyzed with a real-time spectrum analyzer, such as a digital signal processor (DSP), to determine the maximum frequency during the arterial pulse cycle. The maximum frequency, $\omega_{max}$, occurs at the maximum of dE/dt, and in the same way scales with the pulse amplitude. The highest dominant frequency, $\omega_{max}$ can be used for analysis or, if a range of frequencies is present, the first, second, or other moment of the frequency spectrum can be used.

The optical detector 240 output can also be AC coupled and fed into a zero-crossing detector, which provides a count of the number of zero crossing events per unit time (a "zero-crossing rate") and a total count of zero-crossing events during one arterial pulse (the "zero-crossing count"). By properly limiting the size of the detected portion 264, the instantaneous zero-crossing rate is easily shown to be proportional to the rate of modulation of the speckle pattern 260. An algorithm can be applied to detect the rise of the zero-crossing rate above zero, and then to count the number of zero crossings until the zero-crossing rate returns to zero. A threshold slightly above zero can be used, instead of a true zero-crossing rate, to account for system "noise." Alternatively, high frequency noise can be filtered out of a signal from the optical detector 240 or 242. The count can be repeated after the zero-crossing rate again rises above zero until its return to zero. This cycle, including two zero-crossing counts, is taken to correspond to one arterial pulse. The two counts, averaged together, can be proportional to the amplitude of the waveguide oscillatory movement in connection with the arterial pulse, and therefore can also be proportional to the arterial pulse amplitude. An algorithm can be applied to the zero-crossing rate that measures the time at which this rate remains at zero between non-zero episodes. In a sequence of arterial pulses, a relatively longer time can occur between the end of one arterial pulse and the onset of the next one. A relatively shorter time can occur at the maximum pulse pressure, where the pressure stops rising and begins to decrease, in which the zero-crossing rate can be zero momentarily.

In some implementations, the signal dE/dt can be passed through an integrating circuit and integrated over the time from its rise above zero until its return to zero. This time corresponds to the half cycle of the arterial pulse, which can be determined by separately measuring a time-averaged value of dE/dt to determine when it departs from and returns to zero. The resulting integration can be proportional to the amplitude of the waveguide oscillatory movement, and therefore can also be proportional to the arterial pulse amplitude. This integration of the first derivative of a subject's position over a specified time period can yield a result proportional to the change in position during the specified time period.

Figure 10A:
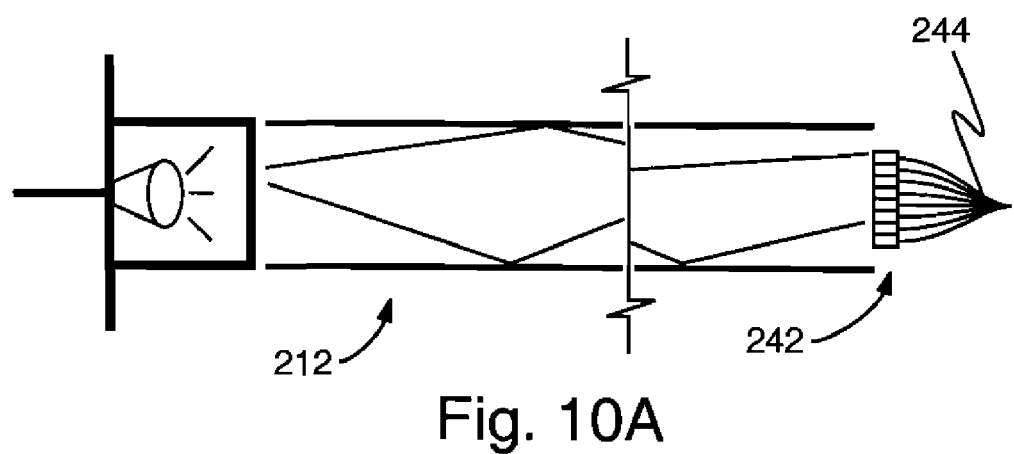
FIGS. 10A, 10B, and 10C depict implementations of the optical sensing system including an optical detector with a plurality of optical detection regions.
Figure 10B:
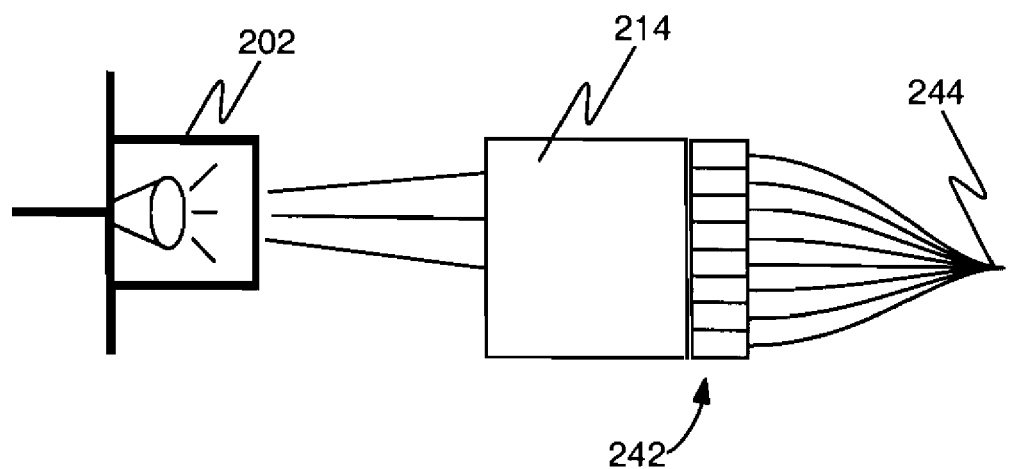
Figure 10C:
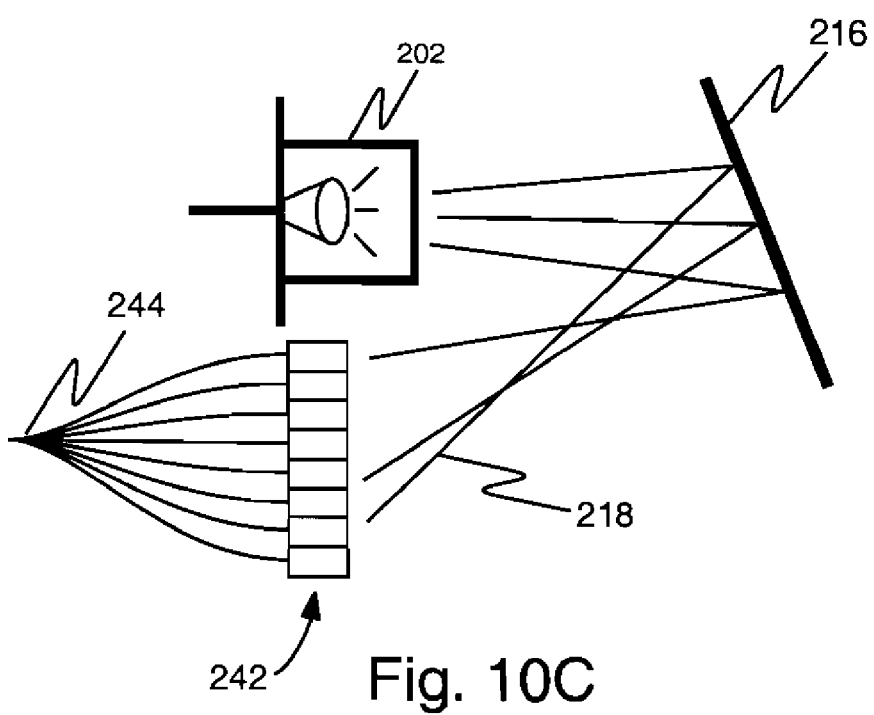

In some implementation, as shown in FIGS. 10A, 10B, and 10C, a plurality of optical detection regions 244 can be used. These optical detection regions 244 can be part of an optical detector 242 that contains a number of discrete optical detection regions 244. For example, optical detector 242 can be a CCD (Charge-Coupled Device) or CMOS (Complementary Metal-Oxide-Semiconductor) detector. Each optical detection region 244 can be configured to only receive a restricted portion of a speckle pattern 260, for example, as shown in FIGS. 10A, 10B, and 10C. Using a plurality of optical detection regions 244 one can obtain data that more reliably represents the relative amplitudes of a series of pulse pressure waveforms. In some implementations, the output from a plurality of optical detection regions 244 can each be AC coupled and fed into a zero-crossing detector. The electrical signals 420 corresponding to the different optical detection regions 244, as shown, for example, in FIG. 13, can be compared at the end of each arterial pulse or at the end of each blood pressure measurement cycle to determine which has the highest signal quality. The quality of an electrical signal 420 can also be determined by detecting a zero-crossing count for each signal. For example, the electrical signal 420 with the highest count may be considered to have the highest signal quality. The different zero-crossing counts for each of the different detectors (or a subset of different detectors) can also be averaged for each arterial pulse to produce a more reliable estimate of the pulse amplitude.

In some implementations, the output from a plurality of optical detectors can each be coupled to a differentiating circuit to measure dE/dt. The different values of dE/dt corresponding to the different detectors can be compared at the end of each arterial pulse or at the end of each blood pressure measurement cycle to determine which has the highest signal quality. For example, the one with the highest value of $dE/dt_{max}$ may be considered to have the highest signal quality. The plurality of different values of dE/dt corresponding to the different detectors (or a subset of different detectors) can also be averaged for each arterial pulse to produce a more reliable estimate of the pulse amplitude.

In some implementations, a CCD (Charge-Coupled Device) or CMOS (Complementary Metal-Oxide-Semiconductor) detector can be used as either a single optical detector 240 or as a plurality of optical detection regions 244. A typical CCD or CMOS detector can have over 1 million pixels, and those in consumer grade digital cameras may have up to 8 million or more pixels in a 1-2 cm rectangular sensor. Each pixel, or separately addressable sensing region, may function as a separate optical detection region 244. "Binning" can also be used to effectively enlarge the detector sensing areas by combining the outputs of an N×M group of pixels (e.g., 2×2, 2×3, 3×3, etc). In some implementations, the size of the detected portion 264 for each optical detection region 244 can be dynamically adjusted by "binning." For example, during the life of a sensor the optical characteristics of the optical refractor 212, 214, or 216 can change and the size of the "binned" group of pixels can be dynamically adjusted during the life of the optical sensing system 104 to re-optimize the size of the detected portion 264. In some implementations, each group of pixels acting as a optical detection region 244 can have the same or different sizes, which can be optimized depending upon the portion of the speckle pattern 260 received by that group of pixels. The use of a CCD or CMOS optical detector 240 or 242 can allow for a device without an optical aperture placed between the optical element and the CCD or CMOS optical detectors because the small size (typically 2-5 microns across) of CCD and CMOS pixels result in an automatic restriction in the area of the detected portion 264 of the speckle pattern 260.

Figure 13:
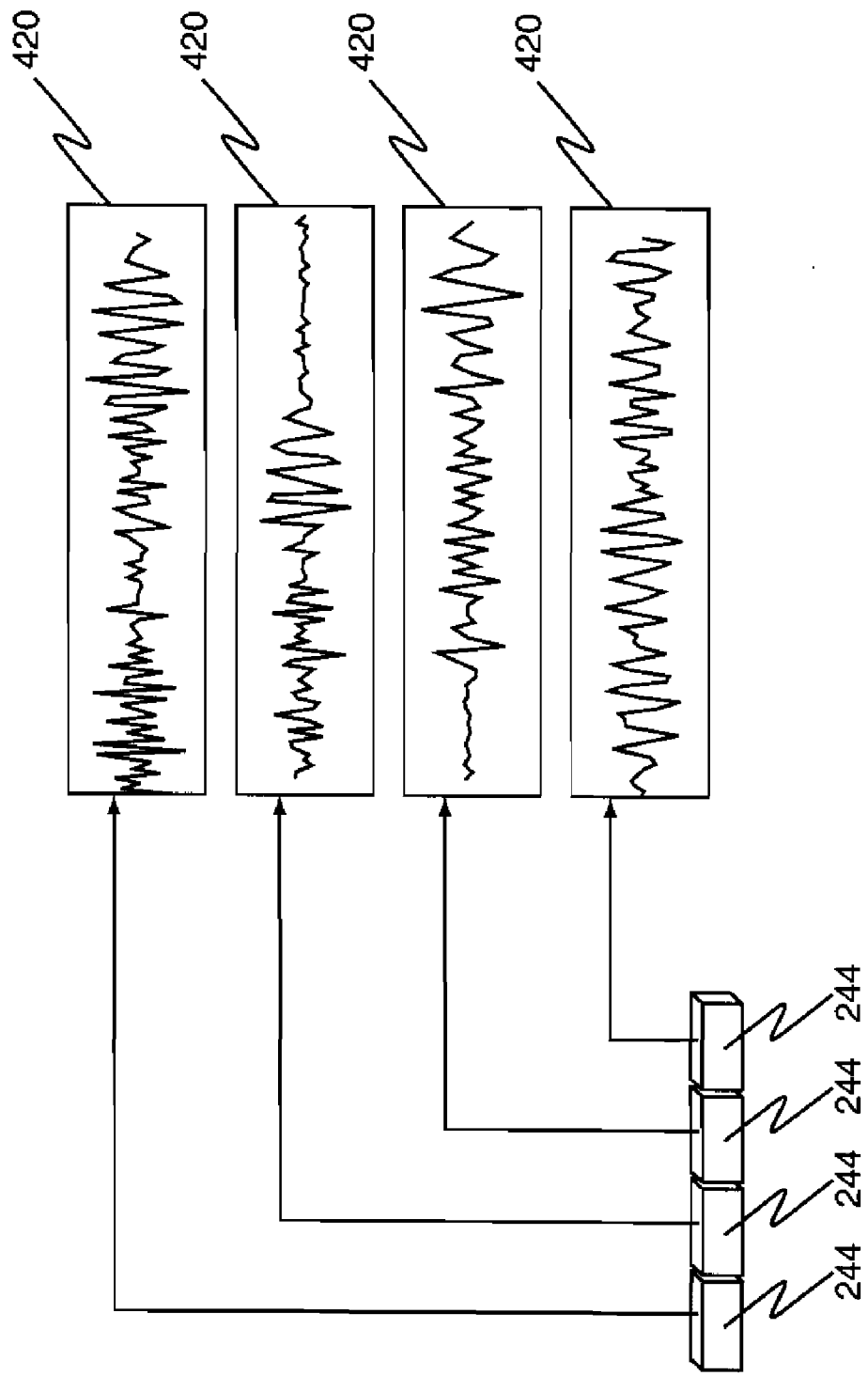
FIG. 13 depicts an implementation of an optical detector having a plurality of optical detection regions each producing electrical signals.

In some implementations, the plurality of CCD or CMOS detectors can be in a 1×N array of either individual pixels or binned combinations of pixels. For example, FIGS. 10A, 10B, and 10C depict a 1×8 array and FIG. 13 depicts a 1×4 array. Furthermore, as shown in FIG. 13, digital signal processing can be performed on each of the N separate digital outputs 420. Each digital output 420 can contain information on the modulation of the optical pattern in a different detected portion 264 of the speckle pattern 260 observed by each optical detection region 244. Each digital signal processing analysis can provide a real-time assessment of the modulation rate (analogous to dE/dt) in one of the detection regions, and can be used to determine the maximum modulation rate during each arterial pulse. The N measurements can be averaged for each arterial pulse to produce a more reliable estimate of the pulse amplitudes and of the pulse amplitude envelope.

In implementations using a CCD or CMOS optical detector 240 or 242 (either as a single optical detector or as a plurality of detectors), an average optical detector output level can be set and defined as a "threshold". The individual detector signals can be measured sufficiently often (typically 100-2000 times per second) to resolve the speckle pattern modulation. The actual data rate can be dependent on the characteristic speckle size relative to the detector area(s) and the rate of movement of the optical element in relation to the light source. Each threshold crossing, defined as an occurrence where the difference between a detector output measurement and the threshold is opposite in polarity from that of the subsequent detector measurement and the threshold, can correspond to a "zero-crossing". The threshold crossings can be counted and analyzed in a manner equivalent to the zero-crossing counts described above.

In some implementation, a digital signal processor (DSP) can be used to analyze the output from one or more optical detectors 240 or 244. Various digital signal processing analysis methods can be applied to determine the modulation rates, including, but not limited to, Fast Fourier Transforms (FFT), autocorrelations, and threshold crossings of the digital CCD or CMOS outputs.

In FFT analysis, a signal can be analyzed to determine a mean frequency by the following algorithm:

$$<\omega> = \int \omega \cdot G(\omega) d\omega,$$

where $\omega$ is the angular frequency, $G(\omega)$ is the power spectrum, and $\int(\omega)d\omega$ is normalized to a value of 1.
$G(\omega)$ is determined by the well known convolution:

$$G(\omega) = [\int g(t) \cdot \exp(-j\omega t) dt]^2,$$

where g(t) is the time varying signal, or optical detector output E in this case. During each arterial pulse, the value of $<\omega>$ can rise and fall in proportion to the signal dE/dt described earlier. Therefore a value of $<\omega>_{max}$ can indicate the maximum modulation rate within a given arterial pulse cycle, and can be scaled and used to generate a pulse amplitude envelope for use in determining the systolic, diastolic, and mean arterial pressures.

In some implementations, an autocorrelation method can be used in order to determine the pulse amplitudes and pulse amplitude envelope. In autocorrelation, the signal can be self-correlated according to the relationship:

$$<G(\tau)> = \int g(t) \cdot g(t-\tau) dt,$$

where $G(\tau)$ is the autocorrelation function at time delay=$\tau$, and g(t) is the time varying signal. The value of G(0) is equal to the mean square of the signal amplitude. The frequency spectrum is simply a convolution of the autocorrelation function, such that:

$$G(\omega)=(1/2\pi)\cdot\int G(\Sigma)\cdot\exp(-j\omega\tau)d\tau.$$

The determination of the mean frequency of a time varying signal using an autocorrelation method has been described previously and is not presented in further detail here. This calculation of $G(\omega)$ is used to calculate the mean frequency according to the same formula as in FFT analysis:

$$<\omega>=\int \omega \cdot G(\omega) d\omega$$

In some implementations, the maximum value of dE/dt can be calculated for each arterial pulse during a time interval when the pressure in the blood pressure cuff is steadily decreased from a level above systolic pressure where the arterial pulse is absent. The onset of each pulse is detected during the time interval by measuring and recording the periodic increase of dE/dt. For each pulse, the maximum value of dE/dt ($dE/dt_{max}$) can be recorded as a dimensionless number, and the cuff pressure can also recorded so as to allow for the creation of an envelope of pulse amplitudes in which the ordinate of the chart is $dE/dt_{max}$ instead of oscillation amplitude in mmHg. An algorithm can be applied to this envelope to determine the systolic, diastolic, pulse, and/or mean arterial pressures.

In some implementations, the zero-crossing count of the AC coupled optical detector output can be tallied for each arterial pulse during a time interval when the pressure in an inflatable cuff 120 is steadily decreased from a level above systolic pressure where the arterial pulse is absent. A series of arterial pulses can be detected during the time interval, and for each pulse the zero-crossing count can be measured and recorded. For each pulse, the count (or average of the two counts corresponding to the rise and fall of the arterial pulse) can be recorded, and the cuff pressure can also be recorded so as to allow for the creation of an envelope of pulse amplitudes in which the ordinate of the chart is the zero-crossing count instead of oscillation amplitude in mmHg. An algorithm can be applied to this envelope to determine the systolic, diastolic, pulse and/or mean arterial pressures.

In some implementations, the time interval between pulses can be measured during a series of detected arterial pulses and used to determine heart rate.

In some implementations, as the cuff pressure is decreased, the systolic pressure can be determined to be an inflatable cuff 120 pressure at which the first evidence of modulation of the speckle pattern occurs (i.e., the rise of the zero-crossing rate above zero, or the first appearance of a non-zero value for dE/dt). In some implementations, the diastolic pressure can be determined to be an inflatable cuff 120 pressure at which a predetermined characteristic of the modulation of the speckle pattern occurs. For example, the last detected arterial pulse, where the zero-crossing rate last has a non-zero value, or where the last non-zero value for dE/dt occurs and after which dE/dt remains at zero while the cuff pressure is further decreased, may be taken as the diastolic pressure. Or the appearance of the first arterial pulse in a sequence of declining arterial pulses where the value of $dE/dt_{max}$ is 50% of the maximum value of $dE/dt_{max}$ (i.e., the highest point on the envelope of pulse amplitudes). In some implementations, the mean arterial pressure can be determined to be an inflatable cuff 120 pressure corresponding to the arterial pulse event at which the maximum zero-crossing count or the maximum value of $dE/dt_{max}$ occurs (i.e., the highest point on the envelope of pulse amplitudes).

In some implementations, the systolic pressure can be calculated to be at some pressure below the cuff pressure at which the first evidence of modulation of the speckle pattern occurs during cuff deflation, based on an empirically determined algorithm that calculates the contribution of some amount of artifact in the arterial pulses acting against the optical sensing system 104, together with other artifact related to the electrical noise and to the modulation of the speckle pattern.

In some implementations, the diastolic pressure can be calculated as some pressure above the cuff pressure at which a predetermined characteristic of modulation of the speckle pattern occurs, based on a corresponding algorithm that calculates the contribution of artifact from the arterial pulses acting against the optical sensing system 104, and other artifact.

In some implementations, a baseline measurement of blood pressure measurement is determined (the "Baseline") and subsequent blood pressure measurements are estimated based upon a continuous monitoring of a vital sign. For example, the baseline blood pressure reading can be obtained using the relative pulse amplitudes of a series of pulses obtained by measurement of $dE/dt_{max}$ or the zero-crossing count as described above, and using either one optical detector 240, a plurality of optical detection regions 244, a CCD sensor array, or a CMOS sensor array. Then the sensor fixation device 102 can then be adjusted to a pressure level with a known (by virtue of said measurement of blood pressure already performed) pulse amplitude (the "Reference Amplitude"), and the arterial pulse amplitude can be measured continuously and compared to the reference amplitude. Any subsequent pulse amplitude measurement that differs from the reference amplitude can be used, with a suitable algorithm, to quantitatively measure blood pressure changes relative to the baseline. In this embodiment, the method's primary purpose is continuous or periodic monitoring of blood pressure changes relative to a Baseline value. In some implementations, the Baseline blood pressure measurement can be determined by other standard methods, such as the auscultatory method.

In some implementations, a pulse waveform morphology can be determined by measuring the time-varying value of dE/dt. The morphology of the pulse waveform can be represented by the curve of dE/dt versus time over the course of an arterial pulse. Alternatively the time varying zero-crossing rate may be used, or the threshold-crossing rate in a digital CCD or CMOS detection system.

Figure 14A:
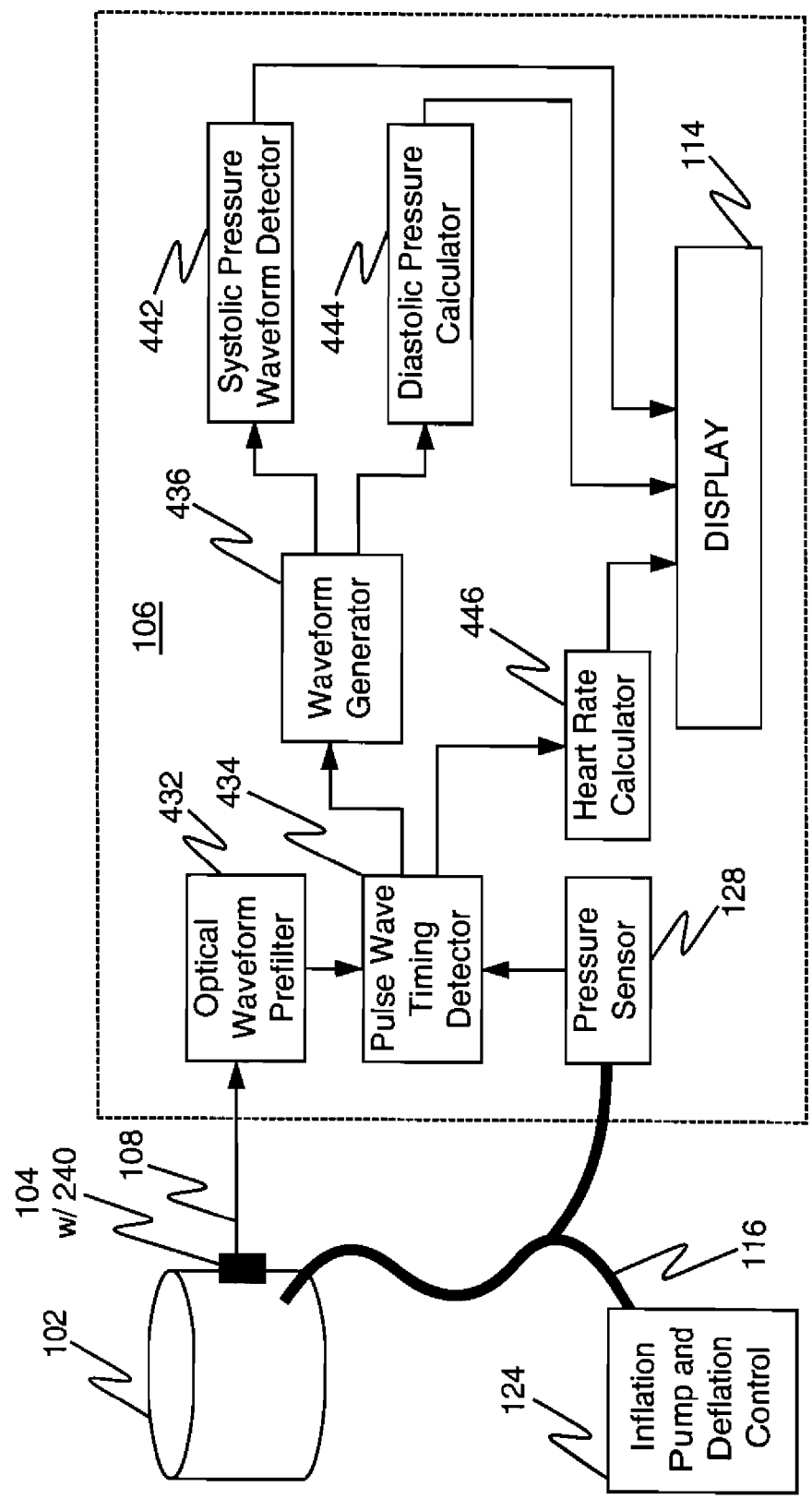
FIGS. 14A, 14B, and 14C depict implementations of the different analytical methods used to determine one or more vital signs by the output unit.
Figure 14B:
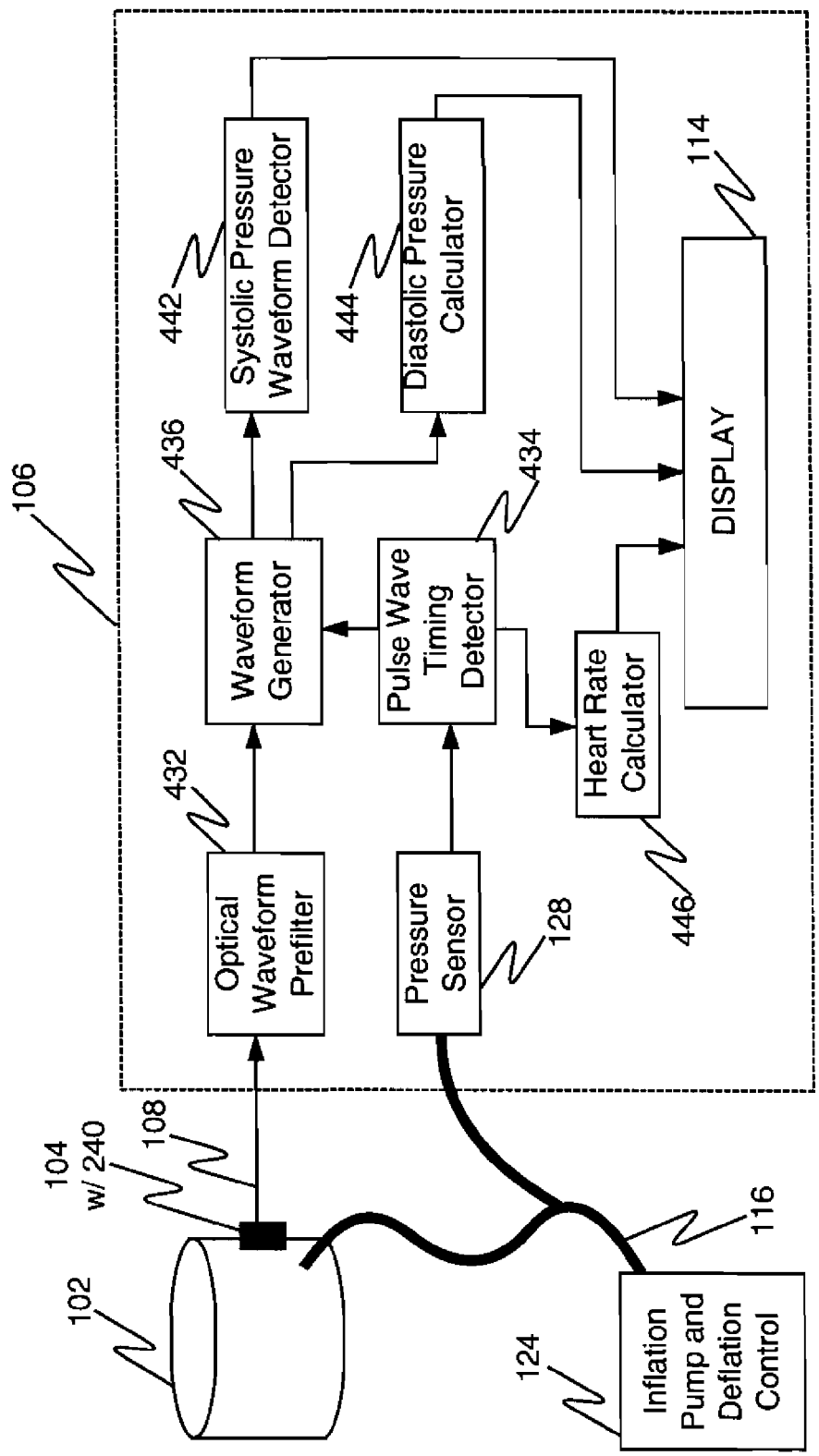
Figure 14C:
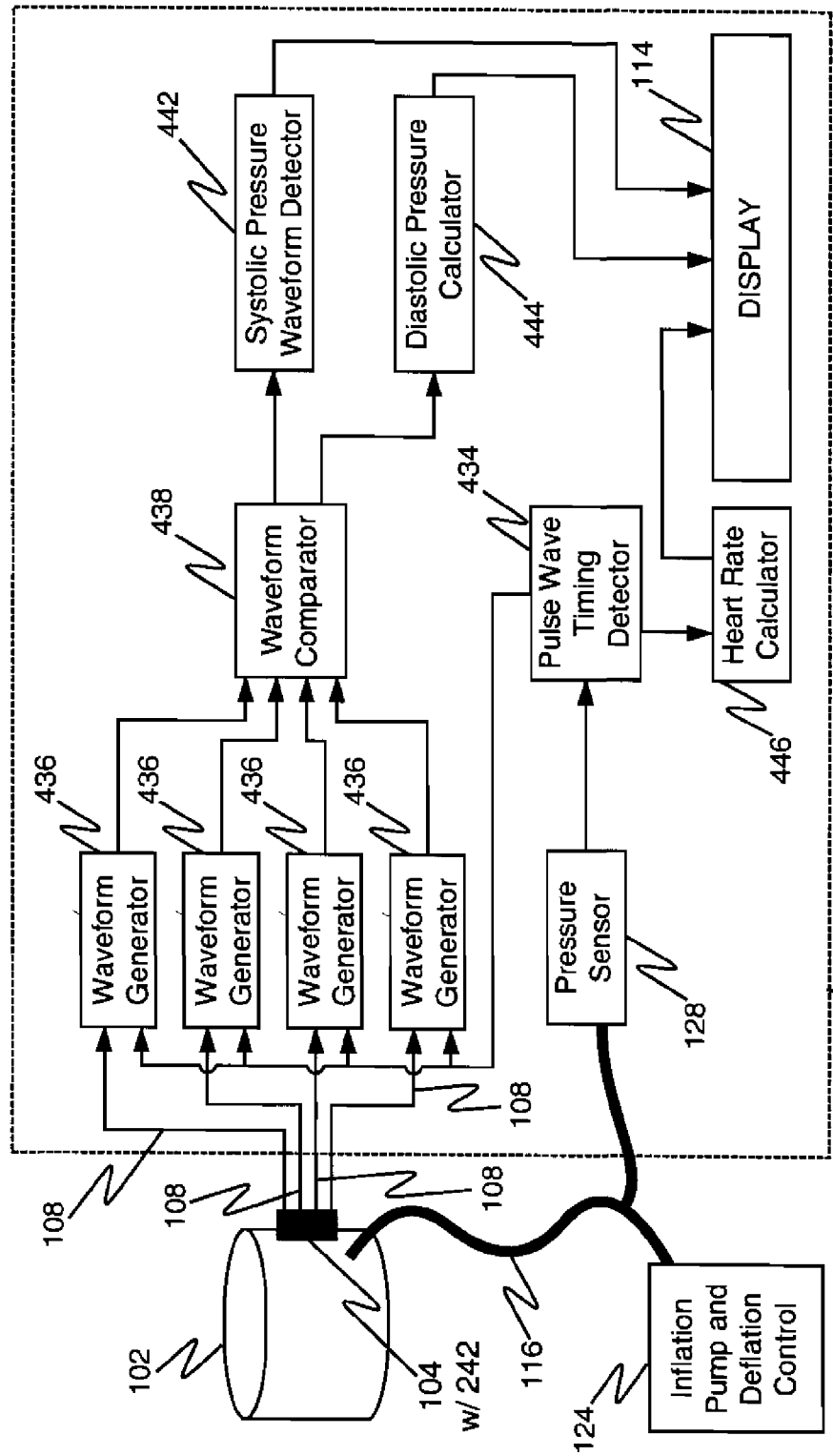

In some implementations, such as shown in FIGS. 14A, 14B, and 14C, the output unit 106 can determine a vital sign by one or more of the above described techniques. For example, the output unit 106 can determine an amplitude, a magnitude and/or a waveform of one or more arterial pulses in a waveform generator 436. In some implementations, the output unit 106 can include a systolic pressure waveform detector to determine a systolic pressure for a subject based upon a determined amplitude, magnitude and/or waveform and a pressure applied to the subject, which can be detected (e.g., a pressure detected in an inflatable cuff by a pressure sensor). In some implementations, the output unit 106 can include a diastolic pressure calculator to determine a diastolic pressure for a subject based upon a determined amplitude, magnitude and/or waveform and a pressure applied to the subject, which can be detected (e.g., a pressure detected in an inflatable cuff by a pressure sensor 128). In some implementation, a heart rate calculator 446 can determine a heart rate from either a determined arterial pulse waveform from the optical signal or from pressures detected in an inflatable cuff by a pressure sensor 128. In some implementations, the output unit 106 can include a pulse wave timing detector 434, which can ensure that each arterial pulse detected by the optical sensing system 104 corresponds to a pulse detected by an inflatable cuff pressure sensor 128. In some implementations, the pulse wave timing detector 434 provides data to the waveform generators 436 to ensure that each waveform generator 436 determines a waveform consistent with pulses detected by an inflatable cuff pressure sensor 128.

In some implementations, such as shown in FIG. 14C, the output unit 106 can determine an amplitude, a magnitude and/or a waveform of one or more arterial pulses for each optical detection region 244 in a series of waveform generators 436. In some implementations, the output unit 106 can include a waveform comparator 438 to compare the plurality of amplitudes, magnitudes, and/or waveforms. The waveform comparator 438 can select the better optical detection regions 244, average the signals from two or more of the optical detection regions, or otherwise compute a single amplitude, magnitude, and/or waveform based on the data from the plurality of optical detection regions 244. In some implementation, a heart rate calculator 446 can determine a heart rate from either a single waveform from the waveform comparator 438 from the optical signal or from pressures detected in an inflatable cuff by a pressure sensor 128.

A number of implementations have been described. Nevertheless, it will be understood that various modifications can be made without departing from the spirit and scope of the invention. Accordingly, other implementations are within the scope of the following claims.

What is claimed is:

1. A vital sign measurement device comprising:
   a sensor fixation device adapted to be placed against an anatomical location of a subject, within which is an artery;
   an optical sensing system comprising an optical source, an optical refractor, and an optical detector, all of which are held by the sensor fixation device and move with movement of the sensor fixation device, wherein the optical sensing system is at least in part positioned on a cantilevered support;
   a sensor pad held by the sensor fixation device so that it is placed against the anatomical location when the sensor fixation device is placed against the anatomical location, wherein at least a part of the optical sensing system is positioned between the sensor pad and the cantilevered support such that a movement of the sensor pad corresponding to an arterial pulse results in a pressing portion of the sensor pad pressing against at least one portion of the optical sensing system to cause a movement, bending, or compression of the at least one portion of the optical sensing system relative to other portions of the optical sensing system resulting in a change in an optical signal received by the optical detector; and
   an output unit that receives, from the optical sensing system, an input indicative of movement corresponding to an arterial pulse and that generates, using the input, a measure of the vital sign.

2. The vital sign measurement device of claim 1, wherein the sensor fixation device is an inflatable cuff.

3. The vital sign measurement device of claim 1, further comprising a pressure sensor to detect a pressure applied to the anatomical location, wherein the output unit receives, from the pressure sensor, a pressure input indicative of the pressure applied to the anatomical location, wherein the output unit generates the vital sign using the input from the optical sensing system and the pressure input.

4. The vital sign measurement device of claim 1, wherein the anatomical location of the subject is an upper arm, and the sensor fixation device is configured so that the optical sensing system is positionable to sense movement due to a pulse of a brachial artery.

5. The vital sign measurement device of claim 1, wherein the anatomical location of the subject is a wrist, and the sensor fixation device is configured so that the optical sensing system is positionable to sense movement due to a pulse of a radial artery.

6. The vital sign measurement device of claim 1, wherein the anatomical location of the subject is an ankle, and the sensor fixation device is configured so that the optical sensing system is positionable to sense movement due to a pulse of one or more arteries in the ankle.

7. The vital sign measurement device of claim 1, wherein the optical refractor is a compressible waveguide.

8. The vital sign measurement device of claim 1, wherein the optical refractor is a flexible waveguide.

9. The vital sign measurement device of claim 1, wherein the optical source and the optical refractor are configured to produce a speckle pattern output.

10. The vital sign measurement device of claim 9, wherein the optical detector is positioned to detect a portion of the speckle pattern output and generate therefrom a signal indicative of optical energy received within the detected portion of the speckle pattern output.

11. The vital sign measurement device of claim 10, wherein the optical sensor further comprises a spatial optical occluder component that prevents the optical detector from receiving a portion of the speckle pattern output.

12. The vital sign measurement device of claim 10, wherein the optical detector comprises an optical energy receiving portion having a smaller surface area than the speckle pattern output.

13. The vital sign measurement device of claim 12, wherein the surface area of the optical energy receiving portion is less than 100 times an average speckle size.

14. The vital sign measurement device of claim 1, wherein the optical source is a coherent light source.

15. The vital sign measurement device of claim 1, wherein the vital sign is at least one of a heart rate, an arterial pulse waveform, a systolic blood pressure, a diastolic blood pressure, a mean arterial blood pressure, a pulse pressure, or an arterial compliance.

16. The vital sign measurement device of claim 1, wherein the output unit generates a measure of the vital sign using a signal indicative of the optical signal received by the optical detector.

17. The vital sign measurement device of claim 1, further comprising a display to depict a vital sign measurement generated by the output unit.

18. The vital sign measurement device of claim 1, further comprising an alarm system to produce a human detectable signal when a vital sign measurement generated by the output unit meets a predetermined criteria.

19. The vital sign measurement device of claim 1, further comprising a spring attached to at least a portion of the optical sensing system to counter a force from the arterial pulse and to return the sensor pad to an initial state after the arterial pulse.

20. The vital sign measurement device of claim 1, further comprising a pressure imparting device adapted to be placed against a second anatomical location of a subject proximal to the anatomical location of the sensor fixation device to allow for arterial pulse detection by the optical sensing system at a position distal to and separated from the pressure imparting device.

21. The vital sign measurement device of claim 1, wherein the optical sensing system and the output unit are adapted to sense a pulse amplitude of the arterial pulse from the movement, bending, or compression of at least one portion of the optical sensing system relative to other portions of the optical sensing system resulting in a change in the optical signal received by the optical detector.

22. The vital sign measurement device of claim 21, wherein the optical sensing system is configured to detect optical signals representative of a series of arterial pulses and the output unit is adapted to determine a pulse waveform for each of the series of arterial pulses.

23. A vital sign measurement device comprising:
- a sensor fixation device adapted to be placed against an anatomical location of a subject, within which is an artery;
- an optical sensing system comprising an optical source, a diffuser, and an optical detector, all of which are held by the sensor fixation device and move with movement of the sensor fixation device, wherein the optical sensing system is at least in part positioned on a cantilevered support, the optical sensing system positioned with respect to the sensor fixation device such that an exterior movement of the anatomical location corresponding to an arterial pulse causes a pressing portion of a sensor pad which is located on the cantilevered support to press, bend, or move a fixed portion of the optical sensing system when the sensor fixation device is placed against the anatomical location of the subject, the optical sensing system sensing an arterial pulse from the movement, bending, or compression of at least one portion of the optical sensing system relative to other portions of the optical sensing system resulting in a change in an optical signal received by the optical detector; and
- an output unit that receives, from the optical sensing system, an input indicative of movement corresponding to an arterial pulse and that generates, using the input, a measure of the vital sign.

* * * * *